(12) United States Patent
Saito et al.

(10) Patent No.: US 7,060,499 B1
(45) Date of Patent: Jun. 13, 2006

(54) DNA CONTAINING VARIANT FRT SEQUENCES

(75) Inventors: Izumu Saito, 10-14-1405, Nishigotanda 8-chome, Shinagawa-ku, Tokyo 141-0031 (JP); Yumi Saito, Tokyo (JP)

(73) Assignees: Izumu Saito, Tokyo (JP); Dainippon Sumitomo Pharma Co., Ltd., Osaka (JP)

( * ) Notice: Subject to any disclaimer, the term of this patent is extended or adjusted under 35 U.S.C. 154(b) by 290 days.

(21) Appl. No.: 10/089,380

(22) PCT Filed: Sep. 28, 2000

(86) PCT No.: PCT/JP00/06686

§ 371 (c)(1),
(2), (4) Date: Mar. 29, 2002

(87) PCT Pub. No.: WO01/23545

PCT Pub. Date: May 4, 2001

(30) Foreign Application Priority Data

Sep. 30, 1999 (JP) .................................. 11-280210
Dec. 6, 1999 (JP) .................................. 11-346727

(51) Int. Cl.
*C12N 15/63* (2006.01)
*C12N 5/10* (2006.01)
*C07H 21/04* (2006.01)
*A01K 67/027* (2006.01)
*A61K 48/00* (2006.01)

(52) U.S. Cl. .................. 435/455; 435/468; 435/471; 435/325; 536/24.2; 514/44

(58) Field of Classification Search .............. 536/24.1; 435/325, 455; 800/13; 514/44
See application file for complete search history.

(56) References Cited

OTHER PUBLICATIONS

Dymecki SM. Flp recombinase promotes site-specific DNA recombination in embryonic stem cells and transgenic mice. Proc Natl Acad Sci U S A. Jun. 11, 1996;93(12):6191-6.*
Emanueli et al. Angiogenesis gene therapy to rescue ischaemic tissues: achievements and future directions.Br J Pharmacol. Aug. 2001;133(7):951-8.*
Marshall E. Gene therapy's growing pains. Science. Aug. 25, 1995;269(5227):1050, 1052-5.*
Rissanen et al. Gene therapy for therapeutic angiogenesis in critically ischaemic lower limb—on the way to the clinic. Eur J Clin Invest. Aug. 2001;31(8):651-66.*
Ross et al. Gene therapy in the United States: a five-year status report. Hum Gene Ther. Sep. 10, 1996;7(14):1781-90.*
Rubanyi GM. The future of human gene therapy. Mol Aspects Med. Jun. 2001;22(3):113-42.*
Schwaab et al. Gene therapy of hemophilia. Semin Thromb Hemost. Aug. 2001;27(4):417-24.*
Sigmund CD. Viewpoint: are studies in genetically altered mice out of control? Arterioscler Thromb Vasc Biol. Jun. 2000;20(6):1425-9.*
Verma et al. Gene therapy—promises, problems and prospects. Nature. Sep. 18, 1997;389(6648):239-42.*
Vooijs et al. Flp-mediated tissue-specific inactivation of the retinoblastoma tumor suppressor gene in the mouse. Oncogene. Jul. 9, 1998;17(1):1-12.*
Eck et al. (1996) Goodman & Gilman's The Pharmacological Basis of Therapeutics, 9th Edition, Chapter 5, McGraw-Hill, NY.*
Orkin et al. (1995) Report and recommendations of the panel to assess the NIH investment in research on gene therapy, available through the National Institutes of Health and at http://www.nih.gov/news/panelrep.html.*
Seibler et al., Biochemistry, vol. 36, No. 7, pp. 1740-1747 (1997).
Schlake et al., Biochemistry, vol. 33, pp. 12746-12751 (1994).
Seibler et al., Biochemistry, vol. 37, pp. 6229-6234 (1998).
Umlauf et al., The EMBO Journal, vol. 7, No. 6, pp. 1845-1852 (1988).

* cited by examiner

*Primary Examiner*—Daniel M. Sullivan
(74) *Attorney, Agent, or Firm*—Birch, Stewart, Kolasch & Birch, LLP

(57) ABSTRACT

To provide DNA comprising mutant FRT sequence which causes recombination reaction between two mutant FRT sequences having an identical sequence to each other but does not cause recombination reaction with a wild-type FRT sequence, in the presence of FLP recombinase; and a method for performing high-efficiency, gene insertion or gene replacement. A DNA comprising a mutant FRT sequence. A DNA comprising a mutant FRT sequence possessing (A) causing no specific DNA recombination reaction with wild type FRT, even if FLP recombinase is present, and (B) causing specific DNA recombination reaction with another mutant FRT sequence having an identical sequence thereto in the presence of recombinase FLP; gene replacement method using the DNA in the presence of recombinase FLP; and a specific DNA recombination method, characterized in that a specific DNA recombination reaction is carried out by using two mutant FRT sequences in the presence of recombinase FLP.

21 Claims, 9 Drawing Sheets

Sense strand

```
                       123456 78
wtFRTs   5'-TCGAGGACGT CGAAGTTCCT ATACTTTCTA GAGAATAGGA ACTTCTCCGG AA-3'  (SEQ ID NO: 12)
f22s     5'-TCGAGGACGT CGAAGTTCCT ATACTATCTA GAGAATAGGA ACTTCTCCGG AA-3'  (SEQ ID NO: 14)
f61s     5'-TCGAGGACGT CGAAGTTCCT ATACTTTCTG GAGAATAGGA ACTTCTCCGG AA-3'  (SEQ ID NO: 15)
f72s     5'-TCGAGGACGT CGAAGTTCCT ATACTTTCTA CAGAATAGGA ACTTCTCCGG AA-3'  (SEQ ID NO: 16)
F3s      5'-TCGAGGACGT CGAAGTTCCT ATACTATTTG AAGAATAGGA ACTTCTCCGG AA-3'  (SEQ ID NO: 17)
f2161s   5'-TCGAGGACGT CGAAGTTCCT ATACTCTCTG AAGAATAGGA ACTTCTCCGG AA-3'  (SEQ ID NO: 18)
f2272s   5'-TCGAGGACGT CGAAGTTCCT ATACTATCTA GAGAATAGGA ACTTCTCCGG AA-3'  (SEQ ID NO: 19)
f2151s   5'-TCGAGGACGT CGAAGTTCCT ATACTCTCCA GAGAATAGGA ACTTCTCCGG AA-3'  (SEQ ID NO: 20)
f2262s   5'-TCGAGGACGT CGAAGTTCCT ATACTATCTT GAGAATAGGA ACTTCTCCGG AA-3'  (SEQ ID NO: 21)
f2373s   5'-TCGAGGACGT CGAAGTTCCT ATACTGTCTA TAGAATAGGA ACTTCTCCGG AA-3'  (SEQ ID NO: 22)
```

Anti-sense strand

```
                       876543 21
wtFRTa   5'-CTAGTTCCGG AGAAGTTCCT ATTCTCTAGA AAGTATAGGA ACTTCGACGT CC-3'  (SEQ ID NO: 13)
f22a     5'-CTAGTTCCGG AGAAGTTCCT ATTCTCTAGA TAGTATAGGA ACTTCGACGT CC-3'  (SEQ ID NO: 23)
f61a     5'-CTAGTTCCGG AGAAGTTCCT ATTCTCCAGA AAGTATAGGA ACTTCGACGT CC-3'  (SEQ ID NO: 24)
f72a     5'-CTAGTTCCGG AGAAGTTCCT ATTCTGTAGA AAGTATAGGA ACTTCGACGT CC-3'  (SEQ ID NO: 25)
F3a      5'-CTAGTTCCGG AGAAGTTCCT ATTCTTCAAA TAGTATAGGA ACTTCGACGT CC-3'  (SEQ ID NO: 26)
f2161a   5'-CTAGTTCCGG AGAAGTTCCT ATTCTCCAGA GAGTATAGGA ACTTCGACGT CC-3'  (SEQ ID NO: 27)
f2272a   5'-CTAGTTCCGG AGAAGTTCCT ATTCTGTAGA TAGTATAGGA ACTTCGACGT CC-3'  (SEQ ID NO: 28)
f2151a   5'-CTAGTTCCGG AGAAGTTCCT ATTCTCTGGA GAGTATAGGA ACTTCGACGT CC-3'  (SEQ ID NO: 29)
f2262a   5'-CTAGTTCCGG AGAAGTTCCT ATTCTCAAGA TAGTATAGGA ACTTCGACGT CC-3'  (SEQ ID NO: 30)
f2373a   5'-CTAGTTCCGG AGAAGTTCCT ATTCTATAGA CAGTATAGGA ACTTCGACGT CC-3'  (SEQ ID NO: 31)
```

FIG. 2

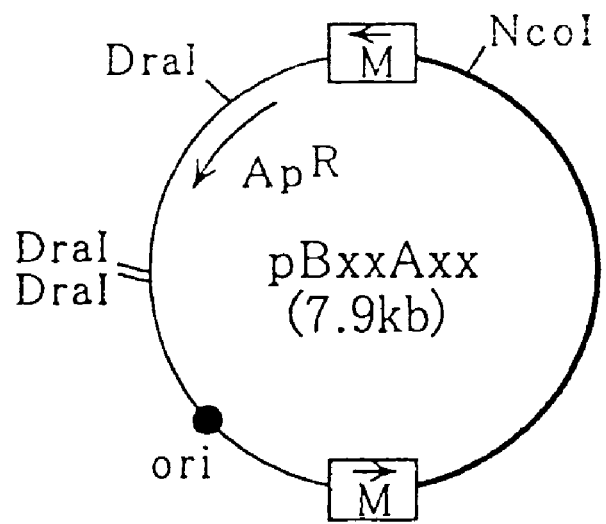
F I G. 3

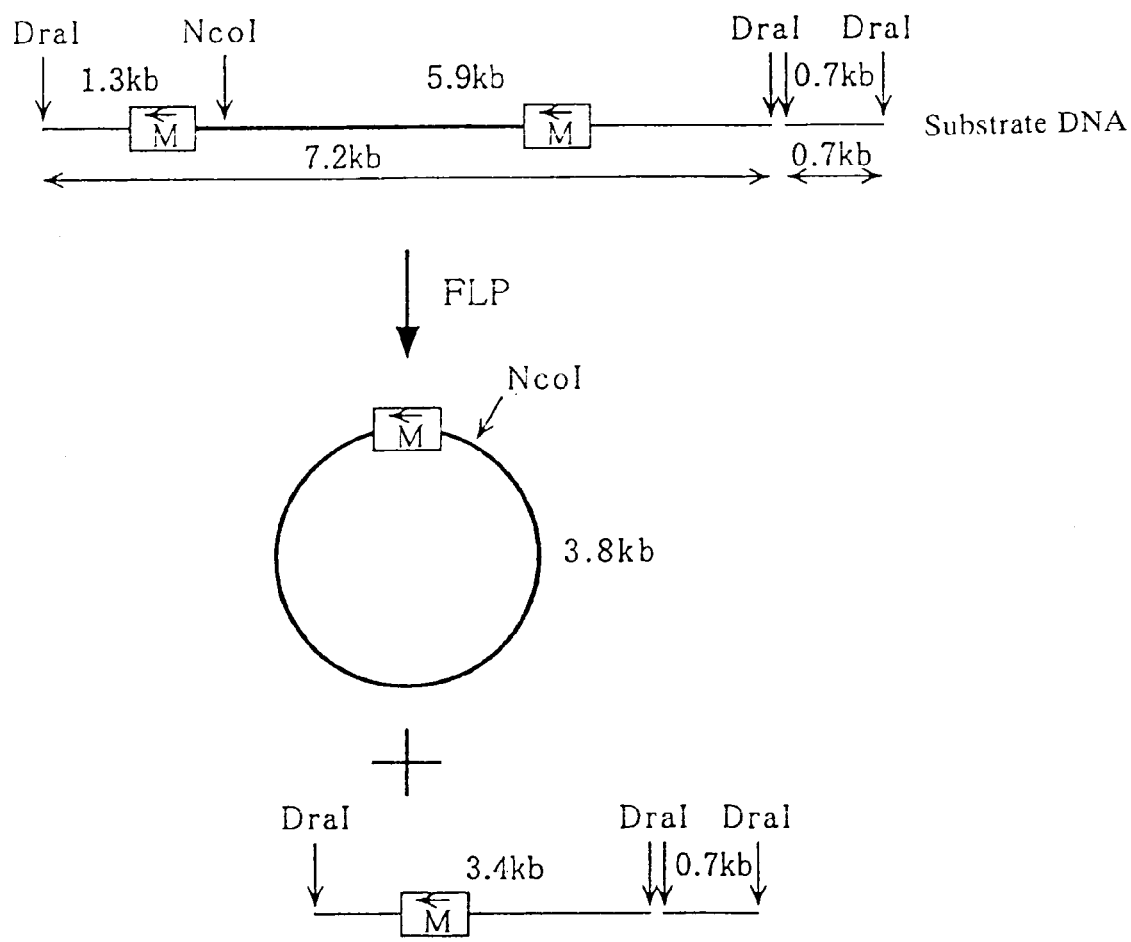
F I G. 4

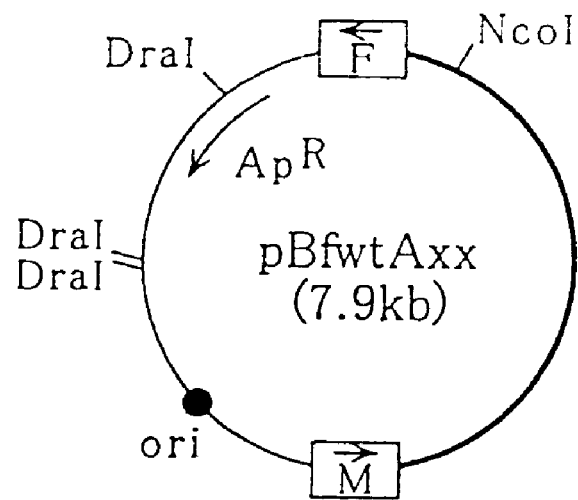
F I G. 6

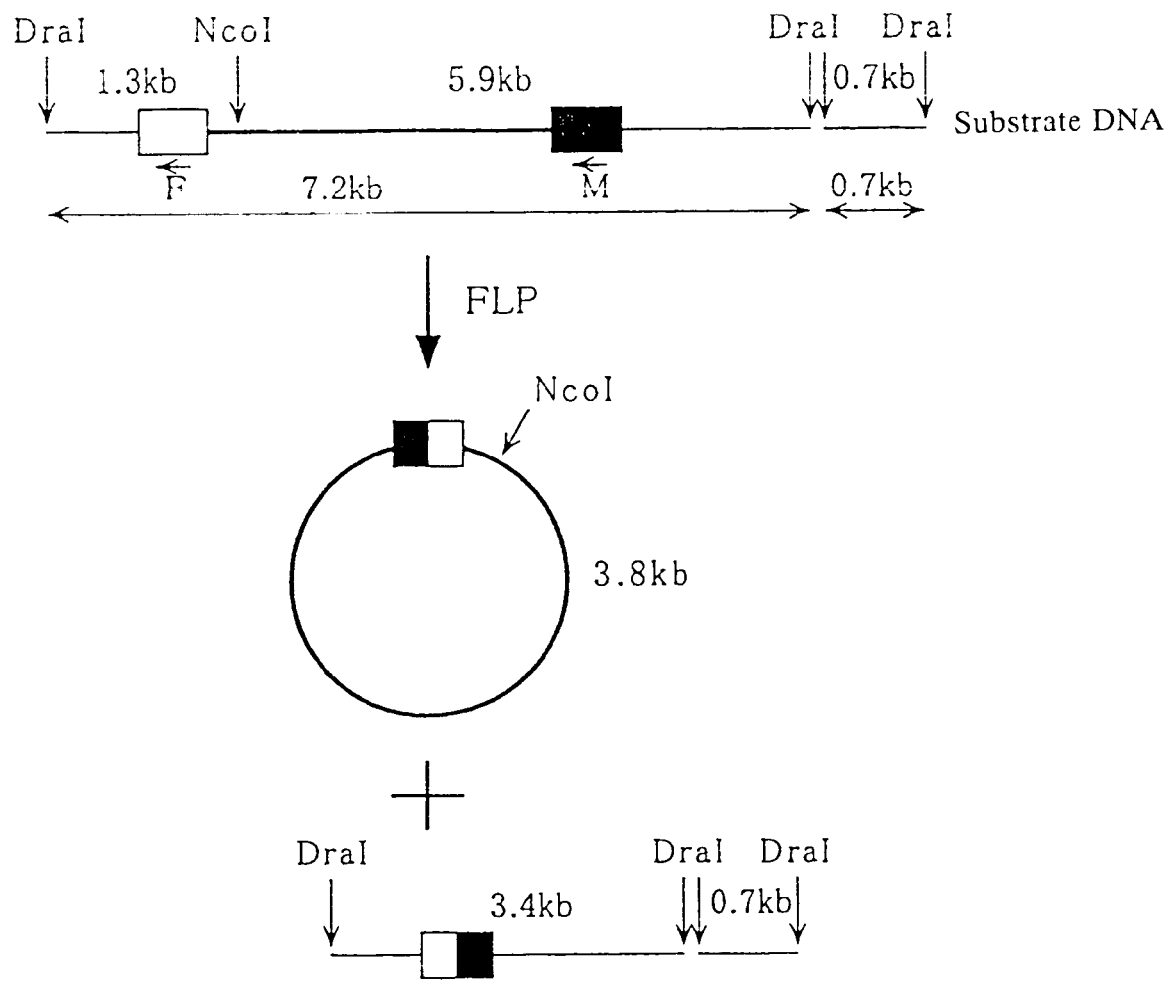
F I G. 7

DNA CONTAINING VARIANT FRT SEQUENCES

This application is the national phase under 35 U.S.C. § 371 of PCT International Application No. PCT/JP00/06686 which has an International filing date of Sep. 28, 2000, which designated the United States of America.

TECHNICAL FIELD

The present invention relates to a DNA comprising mutant FRT sequence and its application. More particularly, the present invention relates to a mutant FRT sequence which causes a specific recombination reaction with the mutant sequences themselves but does not cause a specific recombination reaction with a wild-type FRT sequence, and a method for gene replacement using the mutant FRT sequence, and a method of performing specific DNA recombination.

BACKGROUND ART

FLP recombinase encoded by yeast (*Saccharomyces cerevisiae*) 2μ DNA is a site-specific DNA recombinase that recognizes a particular DNA sequence of 34 nucleotides, which is referred to as FRT sequence, and performs an entire process of cleavage, exchanging and binding of a DNA strand between two FRT sequences, and binding [Babineau et al., *J. Biol. Chem.*, 260, 12313–12319 (1985)]. When two FRT sequences having an identical orientation exist within the same DNA molecule, a DNA sequence flanked by the two FRT sequences is excised by the FLP recombinase, to form a circular molecule (excision reaction). On the other hand, when two FRT sequences exist in the different DNA molecules, one of which is a circular DNA, the circular DNA is inserted into the other DNA molecule via the FRT sequences (insertion reaction).

The insertion reaction and the excision reaction are reversible. However, when two FRT sequences exist within the same DNA molecule, by the insertion reaction, the excision reaction also takes place immediately thereafter. Therefore, the reaction equilibrium leans towards the side of the excision reaction. Therefore, it has been known that the frequency that a given DNA can be inserted into the other DNA molecule by the insertion reaction is very low.

FRT sequence consists of a DNA sequence of 34 bp [Jayaram et al., *Proc. Natl. Acad. Sci.* 82, 5875–5879 (1985)], wherein a sequence of 8 bp flanked by two inverted repeats of 13 bp is referred to as a spacer region. It has been known that DNA recombination is carried out in the spacer region [Umlauf S. W. et al., *EMBO Journal*, 7, 1845–1852 (1988); Lee J. et al., *EMBO Journal*, 18, 784–791, 1999]. FRT sequence (SEQ ID NO: 1) is shown:

```
                   12345678
5'-GAAGTTCCTATAC  TTTCTAGA    GAATAGGAACTTC-3'
                 spacer region
```

It has been found that by changing the nucleotides of the spacer region with nucleotides which are different from inherent FRT sequence (wild-type FRT sequence), i.e. mutant FRT sequence, specific DNA recombination takes place between two mutant FRT sequences but no specific DNA recombination reaction takes place with the wild-type FRT sequence [Schlake T. et al., *Biochemistry*, 33. 12746–12751(1994)]. Further, it has also been shown that genes existing on two different DNA molecules can be replaced in the presence of FLP recombinase by using this mutant FRT sequence in cultured animal cells. In other words, it has been shown that a gene A existing between the mutant FRT sequence and the wild-type FRT sequence on a given DNA molecule can be replaced with a gene B existing between the mutant FRT sequence and the wild-type FRT sequence on the other DNA molecule [Schlake T. et al., *Biochemistry*, 33, 12746–12751 (1994); Seibler J. et al., *Biochemistry*, 36, 1740–1747 (1997)].

A sequence (referred to as "F3," SEQ ID NO: 6) having TATTTGAA in the spacer region has been known as one of known mutant FRT sequences resulting from introduction of a mutation in the spacer region of FRT sequence (Seibler J. et al., supra). Seibler et al. conducted gene replacement on a chromosome of an animal cell using this mutant FRT sequence (F3) and a wild-type FRT sequence. However, the efficiency of gene replacement was as low as 21 to 38% even though cells in which a gene was replaced were enriched by drug selection using a drug-resistance gene before and after gene replacement [Seibler J. et al., *Biochemistry*, 37, 6229–6234 (1998)]. It is thought that this gene replacement efficiency is further lowered if the drug selection is not carried out. In other words, the mutant, F3 of the prior art is an insufficient sequence for performing highly efficient gene replacement reaction, so that a more efficient mutant FRT sequence is desired.

Also, the gene replacement efficiency using the mutant FRT sequence (referred to F5, SEQ ID NO: 7) having the spacer region, CTTGTGAA) is not sufficient in actual use.

DISCLOSURE OF INVENTION

An object of the present invention is to provide a DNA comprising a mutant FRT sequence which causes a recombination reaction between two mutant FRT sequences each having an identical sequence to each other but does not cause recombination reaction with a wild-type FRT sequence, in the presence of FLP recombinase. Another object of the present invention is to provide a method for performing highly efficient, gene insertion or gene replacement in a higher eukaryotic cell such as an animal cell by using a combination of the wild-type FRT sequence with the mutant FRT sequence or a combination of mutant FRT sequences having different sequences in each other, and to apply to gene transfer into a plant or animal cell, preparation of recombinant viruses, gene manipulations in an individual of a plant or animal, and the like.

The present inventors have succeeded in the development of a very sensitive and direct in vitro test method for determining the efficiency of FLP-dependent DNA recombination reaction, in order to search for the desired mutant FRT sequence. We have found a new-mutant FRT sequence which causes recombination reaction between two mutant FRT sequences having an identical sequence to each other, but does not cause recombination reaction with a wild-type FRT sequence, in the presence of FLP recombinase, by determining the efficiency of the DNA recombination reaction of the new mutant FRT sequence resulting from substitution of nucleotides in the spacer region of the FRT sequence with other nucleotides, using this testing method.

Concretely, the present invention relates to:

[1] A DNA comprising a mutant FRT sequence having a sequence resulting from substitution of nucleotides at middle 8-bp (spacer region) in the following wild type FRT sequence (SEQ ID NO: 1) derived from yeast 2μ DNA:

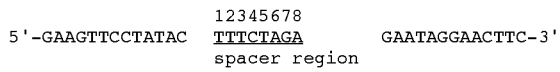

with nucleotide sequences selected from the group consisting of the following (1) to (4):

```
(1)  TCTCTGGA  (f2161)
     (nucleotides 14-21 of SEQ ID NO:2)
(2)  TCTCCAGA  (f2151)
     (nucleotides 14-21 of SEQ ID NO:3)
(3)  TATCTTGA  (f2262)
     (nucleotides 14-21 of SEQ ID NO:4) and
(4)  TTTCTGGA  (f61)
     (nucleotides 14-21 of SEQ ID NO:5)
```

[2] a DNA comprising a mutant FRT sequence having the following properties (A) and (B):

(A) causing no specific DNA recombination reaction with wild type FRT, even if FLP recombinase is present, and (B) causing specific DNA recombination reaction with another mutant FRT sequence having an identical sequence thereto in the presence of recombinase FLP, wherein the mutant FRT sequence consists of a sequence further comprising substitutions of at least one nucleotide in a region other than the spacer region in the mutant FRT sequence defined in the above item [1];

[3] the DNA comprising the mutant FRT sequences according to the above item [1] or [2], wherein no specific DNA recombination reaction is caused with another mutant FRT sequence having a sequence different therefrom even if recombinase FLP is present;

[4] a DNA comprising at least one wild type FRT sequence and at least one mutant FRT sequence defined in any one of the above items [1] to [3];

[5] the DNA according to the above item [4], having a desired gene at between wild type FRT sequence and mutant FRT sequence;

[6] a DNA comprising at least two mutant FRT sequences having different sequences in each other defined in the above item [3];

[7] the DNA according to the above item [6], having a desired gene at between two mutant FRT sequences having different sequences in each other;

[8] a cell which is transformed with the DNA of any one of the above items [4] to [7];

[9] a method for replacing a gene, characterized by reacting the following DNA (a) and DNA (b) in the presence of recombinase FLP, thereby obtaining the following DNA (c):

DNA (a): a DNA having a wild type FRT sequence, a gene A and a mutant FRT sequence of any one of items [1] to [3], in this order;

DNA (b): a DNA having a wild type FRT sequence, a gene B and the same mutant FRT sequence as that of the above DNA (a), in this order;

DNA (c): a DNA in which the gene A is replaced by the gene B in the above DNA (a);

wherein each of the gene A and the gene B is any gene having a sequence different from each other;

[10] a method for replacing a gene, characterized by reacting the following DNA (d) and DNA (e) in the presence of recombinase FLP, thereby obtaining the following DNA (f):

DNA (d): a DNA having two mutant FRT sequences of claim 3 having different sequences in each other, which are referred as mutant FRT sequence 1 and mutant FRT sequence 2, respectively, and a gene A, arranged in the order of the mutant FRT sequence 1, the gene A, and the mutant FRT sequence 2;

DNA (e): a DNA having the mutant FRT sequence 1, a gene B, and the mutant FRT sequence 2, in this order;

DNA (f): a DNA in which the gene A is replaced by the gene B in the above DNA (d); wherein each of the gene A and the gene B is any gene having a sequence different from each other;

[11] the method according to the above item [9] or [10], characterized in that the gene B is not a functional gene;

[12] the method according to the above item [9] or [10], characterized in that the gene A is not a functional gene;

[13] the method according to any one of the above items [9] to [12], wherein DNA (a) or DNA (d) is a chromosomal DNA in a cell, and DNA (b) or DNA (e) is a plasmid DNA or a DNA of double-stranded circular DNA virus;

[14] the method according to any one of the above items [9] to [12], wherein DNA (a) or DNA (d) is a chromosomal DNA in a cell, and DNA (b) or DNA (e) has a property for forming a double-stranded circular DNA by intracellular conversion;

[15] the method according to any one of items [9] to [12], wherein DNA (a) or DNA (d) is a chromosomal DNA from double-stranded DNA virus, and DNA (b) or DNA (e) is a plasmid DNA or a DNA of double-stranded circular DNA virus;

[16] the method according to any one of the above items [9] to [12], wherein DNA (a) or DNA (d) is a chromosomal DNA of double-stranded DNA virus, and DNA (b) or DNA (e) has a property of forming a double-stranded circular DNA by intracellular conversion;

[17] the method according to the above items [15] or [16], wherein the double-stranded DNA virus is adenovirus;

[18] a transgenic animal carrying the DNA of any one of the above items [4] to [7] on chromosomes;

[19] a pharmaceutical comprising the DNA of any one of items [4] to [7]; and

[20] a specific DNA recombination method, characterized in that a specific DNA recombination reaction is carried out in the presence of recombinase FLP, by using two mutant FRT sequences (SEQ ID NO: 32), each resulting from substitution of G with C at the 7th nucleotide of the spacer region in the following wild type FRT sequence (SEQ ID NO:1) derived from yeast 2μ DNA:

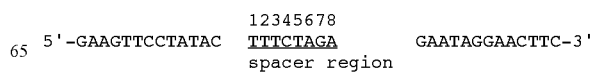

BRIEF DESCRIPTION OF THE DRAWINGS

FIG. 2 shows the sequences of synthesized DNAs comprising a mutant FRT sequence, wherein underlines indicate the nucleotides substituted with those of the wild-type.

FIG. 3 is a schematic view showing the structure of plasmid pBxxAxx, wherein bold line indicates the portion derived from adenovirus, and lightfaced line indicates the portion derived from pBR322, and wherein "M" means a mutant FRT sequence, the arrows above the character indicate the orientation of the FRT sequence, $Ap^R$ is an ampicillin-resistant gene, and ori is a replication origin of *Escherichia coli*.

FIG. 4 is a schematic view showing the principle of the method for determining FLP recombinase-dependent recombination reaction between two mutant FRTs having an identical sequence to each other, wherein bold line indicates the portion derived from adenovirus, and lightfaced line indicates the portion derived from pBR322.

FIG. 6 is a schematic view showing the structure of plasmid pBfwtAxx, wherein bold line indicates the portion derived from adenovirus, and lightfaced line indicates the portion derived from pBR322, and wherein "F" means a wild-type FRT sequence, the arrow above the character indicates the orientation of the FRT sequence, $Ap^R$ is an ampicillin-resistant gene, and ori is a replication origin of *Escherichia coli*.

FIG. 7 is a schematic view showing the principle of the method for determining FLP recombinase-dependent recombination reaction between the wild-type FRT sequence and the mutant FRT sequence, wherein "F" and open box mean the wild-type FRT sequence, and "M" and solid box mean the mutant FRT sequence and the arrows above these characters indicate the orientation of the FRT sequences, and wherein bold line indicates the portion derived from adenovirus and lightfaced line indicates the portion derived from pBR322.

BEST MODE FOR CARRYING OUT THE INVENTION

Figure 1:
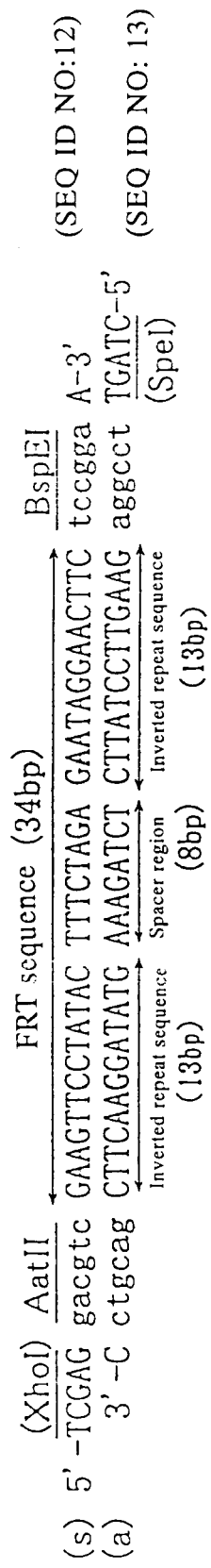
FIG. 1 shows the structure of the synthetic DNA of wild-type FRT sequence, wherein (s) is the sense strand (SEQ ID NO: 12) and (a) is the antisense strand (SEQ ID NO: 13).

The DNA comprising the mutant FRT sequence of the present invention is a DNA comprising a mutant FRT sequence having a sequence resulting from substitution of nucleotides at middle 8-bp (spacer region) in the following FRT sequence (SEQ ID NO: 1) derived from yeast 2μ DNA:

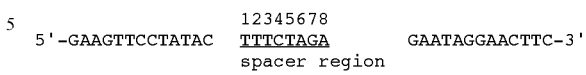

```
           12345678
5'-GAAGTTCCTATAC  TTTCTAGA       GAATAGGAACTTC-3'
                 spacer region
``` with nucleotide sequences selected from the group consisting of the following (1) to (4):

(1) TCTCTGGA (f2161)
    (nucleotides 14–21 of SEQ ID NO:2)
(2) TCTCCAGA (f2151)
    (nucleotides 14–21 of SEQ ID NO:3)
(3) TATCTTGA (f2262)
    (nucleotides 14–21 of SEQ ID NO:4) and
(4) TTTCTGGA (f61)
    (nucleotides 14–21 of SEQ ID NO:5)

wherein said mutant FRT sequence is any one of SEQ ID NOs:2 to 5. Since the DNA of the present invention comprises a sequence selected from the group consisting of the items (1) to (4) mentioned above, there are exhibited excellent properties such that in the presence of FLP recombinase, a recombination reaction between two mutant FRT sequences each having an identical sequence to each other is caused, but no recombination reaction with the wild-type FRT sequence is caused. Further, by using the DNA of the present invention, gene replacement can be performed with an even higher efficiency of gene replacement.

In addition, the DNA comprising a mutant FRT sequence of the present invention may be either an isolated DNA or synthetic DNAs.

The term "FLP recombinase" in the present invention refers to an enzyme which is encoded by yeast (*Saccharomyces cerevisiae*) 2μ DNA and performs site-specific recombination reaction between two FLP recognition sequences (FRT sequences) [Babineau et al., *J. Biol. Chem.*, 260, 12313–12319 (1985)]. A region flanked by two FRT sequences which are positioned in the same orientation can be excised by the FLP recombinase.

The term "FRT sequence" in the present invention refers to the DNA sequence consisting of 34 bp as shown in SEQ ID NO: 1 [Jayaram et al., *Proc. Natl. Acad. Sci.* 82, 5875–5879 (1985)]. The term "spacer region" refers to a 8-bp DNA sequence flanked by two inverted repeats (13 bp) in the above-mentioned FRT sequence. In the present specification, this FRT sequence consisting of 34 bp is especially referred to as a "wild-type FRT sequence."

The term "mutant FRT sequence" in the present invention refers to a DNA sequence resulting from substitution of at least one nucleotide with another nucleotide in the above-mentioned wild-type FRT sequence. The term "mutant FRT sequence resulting from substitution of the spacer region" in the present invention refers to a DNA sequence resulting from substitution of at least one nucleotide with another nucleotide in the 8-bp spacer region of the wild-type FRT sequence.

The DNA comprising a mutant FRT sequence of the present invention is a DNA comprising a mutant FRT sequence which causes the recombination reaction between two mutant FRT sequences having an identical sequence to each other, but does not cause FLP-dependent DNA recombination reaction with the wild-type FRT sequence, among the above-mentioned mutant FRT sequences. Therefore, the mutant FRT sequence of the present invention also encompasses mutant FRT sequences resulting from further substitutions of not only nucleotides of the spacer regions but also nucleotides of their inverted repeat sequences, as long as they satisfy the above-mentioned properties.

Concretely, the DNA comprising a mutant FRT sequence of the present invention may also encompass a DNA comprising a mutant FRT sequence possessing the following properties (A) and (B):

(A) causing no specific DNA recombination reaction with wild type FRT, even if FLP recombinase is present, and (B) causing specific DNA recombination reaction with another mutant FRT sequence having an identical sequence thereto in the presence of recombinase FLP, wherein the mutant FRT sequence consists of a sequence further comprising substitutions of at least one nucleotide in a region other than the spacer region in the mutant FRT sequence.

The DNA encompasses a DNA comprising a mutant FRT sequence possessing a property of causing no specific DNA recombination reaction with the another mutant FRT sequence having a different sequence therefrom even if FLP recombinase is present.

In addition, in the present specification, a DNA consisting of a mutant FRT sequence resulting from deletion or insertion of nucleotides in a region other than the spacer region in the mutant FRT sequence is encompassed by the present invention, as long as the DNA comprises a sequence possessing the properties (A) and (B) mentioned above.

Also, in the present specification, the terms "wild-type FRT sequence" and "mutant FRT sequence" may be collectively simply referred to as "FRT sequence" in some cases.

In the present specification, the phrase "specific DNA recombination reaction in the presence of FLP recombinase" and the phrase "FLP-dependent DNA recombination reaction" have the same meanings, referring to an entire reaction process of cleavage of DNA strands, exchanging and binding of DNA strands occurring between DNAs comprising two FRT sequences, under the conditions of the presence of FLP recombinase.

The DNA comprising a mutant FRT sequences of the present invention includes, but not being particularly limited thereto, for example, a DNA comprising at least one wild-type FRT sequence and at least one of the above-mentioned mutant FRT sequences, and a DNA comprising at least two of the above-mentioned mutant FRT sequences having a different sequence in each other.

Using this DNA, a DNA having a desired gene between the two FRT sequences, namely between the FRT sequence and the FRT sequence can be prepared to use for the method for gene replacement. Such a DNA is also encompassed by the present invention. Concrete examples thereof include a DNA having a desired gene between the wild-type FRT sequence and the mutant FRT sequence, a DNA having a desired gene between the two mutant FRT sequences having a different sequence in each other.

The above-mentioned term "desired gene" may be, but not particularly limited to, a gene encoding protein, structural genes such as promoters or poly(A) sequences, and genes not having a function such as linkers.

In the present specification, the term "gene replacement" refers to substitution of genes each existing on two different DNA molecules. The technical idea of the method of performing gene replacement using a wild-type FRT sequence and a mutant FRT sequence in the presence of FLP recombinase is disclosed in a known literature [Schlake T. et al., *Biochemistry*, 33, 12746–12751 (1994)].

The efficiency of the DNA recombination reaction in the method for gene replacement using of the DNA comprising the mutant FRT sequence of the present invention can be determined by a very sensitive and direct in vitro method for determining an efficiency of FLP-dependent DNA recombination reaction developed by the present inventors.

In summary, this determination method comprises reacting a substrate DNA resulting from insertion of two FRT sequences into a DNA of an appropriate length, for a defined time in the presence of FLP recombinase; digesting the resulting DNA with appropriate restriction enzymes; and determining a reaction efficiency from the sizes of DNA bands separated by electrophoresis. The efficiency of DNA recombination reaction can be quantitatively determined since the amount of the substrate DNA bands before the reaction can be directly compared with the amount of the DNA bands generated by the recombination reaction. The present inventors have already established a method for determining an efficiency of Cre-dependent DNA recombination reaction under the same principle, wherein Cre is another recombinase derived from P1 phage [Lee, G. et al., *Gene* 14, 55–65 (1998)]. This determination method will be described in detail below.

First, DNAs having a wild-type FRT sequence and a mutant FRT sequence resulting from substitution of nucleotide in its spacer region with another nucleotide is synthesized. The method for synthesizing the DNA includes, but not being particularly limited to, PCR method, site-directed mutagenesis and the like. It is desired to use the DNA in the form of a double-stranded DNA prepared by chemically synthesizing complementary single-stranded DNAs using a DNA synthesizer or the like, and thereafter annealing the complementary DNAs. The DNA having FRT sequences is not particularly limited, as long as it contains FRT sequence of 34-bp. It is desired that the DNA contains a recognition sequence for restriction enzymes in addition to the FRT sequence.

Next, the above-mentioned DNA having a wild-type or mutant FRT sequence is ligated to both ends of a DNA fragment of an appropriate length, for instance, a linearized DNA fragment resulting from digestion with restriction enzymes of plasmid pBR322, to prepare a linear DNA fragment having two wild-type FRT sequences, or two mutant FRT sequences each having an identical sequence in each other at both ends. Next, a plasmid in which this DNA fragment is ligated to a DNA fragment of an appropriate length, for instance, an adenovirus-derived DNA fragment, is constructed, and the plasmid is then digested with a restriction enzyme, to prepare a linear substrate DNA. Alternatively, in accordance with the same method, a linear substrate DNA having a wild-type FRT sequence and a mutant FRT sequence is prepared from a plasmid carrying one wild-type FRT sequence.

The method for preparing an enzyme solution containing FLP recombinase is not particularly limited, and can be prepared from yeast, *Escherichia coli*, cultured cells or the like which is engineered to express FLP recombinase. It is preferable to use an extract of cultured cells which have been infected with a recombinant adenovirus capable of expressing FLP recombinase. This is because cells infected with the recombinant adenovirus express the desired protein at a high level.

The above-mentioned substrate DNA is allowed to react with the enzyme solution containing FLP recombinase for a given period of time, and the reaction mixture is then digested with an appropriate restriction enzyme. The resulting DNA bands are analyzed by electrophoresis on agarose gel. In this determination method, the efficiency of recombination between two mutant FRT sequences having an identical sequence to each other or between the wild-type FRT sequence and the mutant FRT sequence can be determined quantitatively at high sensitivity, because the amounts of non-reacted substrate DNA, DNA generated by recombination, and intermediate DNA of the recombination can be directly compared to each other.

The present inventors have hypothesized that the combination of mutations at 2nd nucleotide and from 5th to 7th nucleotides of the spacer region of FRT sequence is particularly important, and proposed the 5 mutant FRT sequences: f2161 (SEQ ID NO: 2), f2151 (SEQ ID NO: 3), f2262 (SEQ ID NO: 4), f2272 (SEQ ID NO: 8), and f2373 (SEQ ID NO: 9). Further, we have also proposed f61 mutant FRT sequence (SEQ ID NO: 5) resulting from substitution only one nucleotide, for the sake of comparison with those resulting from substitution of two nucleotides.

Next, regarding the above-mentioned 6 kinds of the mutant FRT sequences, the efficiency of the recombination reaction between two mutant FRT sequences having an identical sequence to each other has been determined by using the above-mentioned determination system. For the sake of comparison, F3, which is a mutant FRT sequence in the prior art, and two types of mutant FRT sequences resulting from substitution of one nucleotide (see FIG. 2) are similarly determined.

The recombination efficiency in the mutant FRT sequence having F3 sequence of the prior art was about 65% that of the wild-type FRT sequence, showing an inadequate level of recombination efficiency. On the other hand, the mutant FRT sequences f2161 and f2262 of the present invention showed higher recombination efficiencies than that of F3, and each of those of f2151 and f61 showed substantially the same or slightly lower level of recombination efficiency which was still sufficiently usable for practical purposes. Concretely, each of these mutant FRT sequences of f2161, f2262, f2151 and f6 are mutant FRT sequences which can achieve the object of the present invention. Alternatively, f 72 (SEQ ID NO: 32), of which sequence has been already known, showed unexpected results such that the recombination efficiency was twice or more than that of the wild-type FRT sequence. In other words, f72 can be used as a substrate for FLP-dependent DNA recombination reaction which has a higher efficiency than that of the wild-type FRT sequence.

Further, as a desired mutant FRT sequence, a mutant FRT sequence which causes specific recombination reaction with mutant FRT sequences themselves but does not cause any specific recombination reaction with a wild-type FRT sequence can be selected by determining the efficiency of the recombination between the wild-type FRT sequence and the mutant FRT sequence in the same manner.

By the use of the DNA comprising a mutant FRT sequence of present invention, a method for gene replacement having excellent efficiency in gene replacement can be performed. The method for gene replacement is also encompassed in the scope of the present invention.

The method for performing a gene replacement of present invention includes a method for performing a gene replacement (hereinafter referred to as "gene replacement method 1" in some cases) characterized by reacting the following DNA (a) and DNA (b) in the presence of recombinase FLP, thereby obtaining the following DNA (c):

DNA (a): a DNA having a wild type FRT sequence, a gene A and a mutant FRT sequence of the present invention, in this order;

DNA (b): a DNA having a wild type FRT sequence, a gene B and the same mutant FRT sequence as that of the above DNA (a), in this order;

DNA (c): a DNA in which the gene A is replaced by the gene B in the above DNA (a); and a method for performing a gene replacement (hereinafter referred to as "gene replacement method 2", characterized by reacting the following DNA (d) and DNA (e) in the presence of recombinase FLP, thereby obtaining the following DNA (f):

DNA (d): a DNA having two mutant FRT sequences having different sequences in each other, which are referred as mutant FRT sequence 1 and mutant FRT sequence 2, respectively, and a gene A, arranged in the order of the mutant FRT sequence 1, the gene A, and the mutant FRT sequence 2;

DNA (e): a DNA having the mutant FRT sequence 1, a gene B, and the mutant FRT sequence 2, in this order;

DNA (f): a DNA in which the gene A is replaced by the gene B in the above DNA (d).

Here, the gene A and the gene B are any genes each having a sequence different from each other. Each of the gene A and the gene B may not be a functional gene.

In the present specification, the phrase "not (be) a functional gene" means that the gene is a DNA sequence which does not possess any known function or regulatory function of a structural gene. Exemplification of the gene includes linkers and the like.

As concrete examples for the method for gene replacement of the present invention, the gene replacement method 1 (method using a wild-type FRT sequence and a mutant FRT sequence) will be explained. The same can be said for the gene replacement method 2 (method using of a mutant FRT sequence 1 and a mutant FRT sequence 2). In addition, an embodiment where genes on a chromosome of an animal cell are replaced will be explained. However, this method is not limited to gene on a chromosome of an animal cell, and can also be applied to the genomes of animal viruses, chromosome of plant cells, yeast, microorganisms such as bacteria; bacteriophage and the like.

First, a wild-type FRT sequence and a mutant FRT sequence are previously inserted into chromosome of an animal cell. A given gene A may exist between the wild-type FRT sequence and the mutant FRT sequence. In this case, gene replacement will be performed. On the other hand, when the gene A does not exist, gene insertion will be performed.

On the other hand, a gene B to be introduced is previously inserted between the two FRT sequences in a circular DNA molecule resulting from insertion of a wild-type FRT sequence and a mutant FRT sequence (referred to as "wild-type FRT sequence/gene B/mutant FRT sequence").

The "circular DNA molecule" may be, for instance, either a molecule which originally has a circular form, such as plasmid DNA or double-stranded circular DNA virus, or a molecule which will have a double-stranded circular DNA form after the molecule is transferred into a cell according to a conventional method and then converted in the cell.

The above-mentioned circular DNA molecule containing the wild-type FRT sequence/gene B/mutant FRT sequence is transferred into the above-described cell by any known methods, and FLP recombinase is at the same time expressed in the cell by known method, whereby the gene B in the circular DNA molecule is inserted between the wild-type FRT sequence and the mutant FRT sequence on the chromosome of the cell. During this process, when the gene A exists between the two FRT sequences on the chromosome of the cell, gene replacement is performed, resulting from removal of the gene A and insertion of the gene B. When no gene exists between the two FRT sequences on the chromosome, gene insertion is performed. Further, when no gene exists between the two FRT sequences in the circular DNA, the gene A on the chromosome can be removed (gene deletion). Moreover, since two FRT sequences exist on the chromosome even after the removal the gene A, a gene can be again transferred between the two FRT sequences on the chromosome by using another circular DNA molecule having a given gene C between the two FRT sequences. The above-mentioned gene insertion and gene deletion are also encompassed within the scope of the method for gene substitution of the present invention.

As to a method for transferring a DNA molecule into a cell, a method which is generally employed can be used. Examples thereof include physicochemical methods such as electroporation method, calcium phosphate co-precipitation method, DEAE-dextran method, lipofection method, those using a gene gun or the like; and biological methods such as those using circular DNA virus; and the like.

The circular DNA virus depends upon the kinds of cells used, and the virus includes, for instance, papilloma virus, SV40 and the like.

An example of a method for forming a circular DNA molecule after its transfer into a cell includes those using recombinases. The recombinase includes Cre recombinase derived from bacteriophage P1 [Sternberg et al., *J. Mol. Biol.* 150, 467–486 (1981)], R recombinase derived from pSR1 plasmid of *Zygosaccharomyces rouxii* [Matsuzaki et al., *Mol. Cell. Biol.* 8, 955–962 (1988)], FLP recombinase, and the like.

When two FRT sequences are previously inserted into the chromosome of the cell, a cell may be transformed by using, for instance, a plasmid DNA in which two FRT sequences exist.

As the method for transferring a gene in transformation, there is included the above-mentioned physicochemical methods. Further, there may be used a virus possessing a property of inserting a viral genome, such as retrovirus, adeno-associated virus or HIV, into the chromosome of a cell.

The method for expressing FLP recombinase in an animal cell includes a method comprising transferring DNA or RNA having recombinase FLP gene into a cell, and thereafter expressing the recombinase FLP in the cell (recombinase FLP gene-introducing method); a method comprising introducing FLP recombinase protein per se into a cell (recombinase FLP protein-introducing method); and the like.

Examples of the recombinase FLP gene-introducing method include a method comprising transferring DNA or RNA having FLP gene into a cell, by means of the above-mentioned physiochemical methods; or a method using a viral vector. The viral vector includes adenovirus, vaccinia virus, herpes virus, EB virus and the like, and adenovirus is preferable from the viewpoint of a high gene transfer efficiency.

Advantages of the method for gene replacement on a chromosome of the cell using the DNA comprising a mutant FRT sequence of the present invention are such that its efficiency is high, and that a gene can be inserted in a specified site of chromosome. The gene transfer to a specified site of the chromosome is particularly important in order to obtain transformed cells.

The reasons therefor are as follows. An insertion site of a desired gene on a chromosome is random in a usual transformation method using DNA (method other than homologous recombination) or a conventional method using a viral vector such as retrovirus or adeno-associated virus, so that there are great differences in the expression level of the desired gene and its stability on the chromosome depending on the insertion site. Therefore, a very large number of cell lines are required to be screened in order to obtain a transformed cell line capable of expressing the desired gene stably (for a long period of time) and at a high level. Moreover, there is required a complicated procedure such that this screening must be repeated for each gene, i.e., for each transformation. On the other hand, according to the method for gene replacement of the present invention, once a stable cell line capable of expressing the gene at a high level is obtained using expression of a given gene flanked by two FRT sequences as an index, a stable cell line capable of expressing the desired gene at a high level can easily be obtained even when any given gene is transferred. Moreover, since its efficiency is very high, the desired cell line can be obtained in a short period of time simply by cloning manipulation of the cell without necessitating procedures of drug selection which are usually required. The cell line subjected to transfer is not particularly limited, and it is particularly effective in the transformation of ES cell or the like used for preparing a transgenic animal.

Cells transformed by the above-mentioned DNA comprising a mutant FRT sequence are also encompassed within the scope of the present invention.

The method for gene replacement of the present invention can be applied not only to cultured cells but also to animal individuals. A method for expressing a particular foreign gene in an animal individual includes a technique for a transgenic animal. However, in order to prepare a transgenic animal by a usual method, there are necessitated complicated procedures in which a large number of transgenic animals is obtained for the first time by firstly preparing ES cell or the like capable of expressing a desired gene, thereafter developing the ES cell or the like in the abdomen of a foster mother, screening the progenies using the expression of the desired gene as an index, and cross-breeding animal individuals expressing the desired gene. Therefore, there arise a defect that it takes a very long period of time for the preparation of a transgenic animal expressing the desired gene. Usually, these manipulations require from a half year to one year.

When the method for gene replacement of the present invention is employed, the preparation of a transgenic animal for individual genes are not necessitated, once a transgenic animal for gene transfer is prepared. The term "transgenic animal for gene transfer" refers to an animal resulting from insertion of the mutant FRT sequence and the wild-type FRT sequence on a chromosome. The preparation of the transgenic animal is performed in the same manner as any conventional method for preparing a transgenic animal. In addition, drug-resistance gene such as neomycin-resistance gene may be inserted between the two FRT sequences for selection by the drugs. By transferring DNA (a), which is DNA resulting from insertion of a desired gene between a wild-type FRT sequence and a mutant FRT sequence, namely a circular DNA having sequences in the order of the wild-type FRT sequence, the gene A and the above-mentioned mutant FRT sequence, and FLP recombinase into the animal for gene transfer, the desired gene is inserted into the chromosome of the tissue or cell resulting from transfer of both of the DNA (a) and FLP recombinase, whereby the gene thereof can be expressed. The transfer of DNA (a) and FLP recombinase into an individual animal can be sufficiently performed by a known method such as liposome method, a known method using a viral vector, or genetic gun, and the like.

When the method of the present invention is used, DNA (a) depending upon the genes may be used even when different genes are introduced, so that the preparation of the transgenic animal which requires a very long period of time is not needed. The present invention also encompasses a transgenic animal having a DNA comprising the above-mentioned mutant FRT sequence on the chromosome. Since the transgenic animal of the present invention carries the above-mentioned DNA comprising the mutant FRT sequence of the present invention on the chromosome, the transgenic animal has an excellent property in that the transgenic animal can be widely used for transfer of various genes.

Further, a desired gene can be inserted only into a desired organ or tissue, simply by locally transferring both of DNA (a) and FLP recombinase.

The method for gene replacement of the present invention can also be used for the preparation of a recombinant virus. Viruses include DNA viruses, and the DNA viruses include adenovirus; herpes viruses such as herpes simplex virus, EB virus and cytomegalovirus; vaccinia virus; poxviruses such as Canary-poxviruse; baculoviruses for insect; and the like. Alternatively, viruses include RNA viruses which are especially preferable for the preparation of retroviruses.

When the retrovirus vector is prepared, a high-titer virus-producing cell is selected for each retrovirus vector that produces each gene. According to the method for gene replacement of the present invention, it can be thought that once a high-titer virus-producing cell line expressing a marker gene is established, the marker gene on the chromosome of the cell line is replaced with a desired gene, whereby a high-titer cell line can be easily obtained.

A concrete method for preparation of recombinant virus according to the method for gene replacement of present invention will be explained by taking the preparation of recombinant adenovirus as an example. The method for preparing recombinant adenovirus in the prior art is a method comprising transforming a cell such as 293 cell with a plasmid vector or cosmid vector resulting from insertion of an adenovirus genome and a desired gene, cloning the recombinant virus generated by homologous recombination, and thereafter screening and proliferating the desired virus. This method requires a long period of time of labor.

According to the preparation of the recombinant virus by the method for gene replacement of the present invention, a desired recombinant virus can be prepared in a shorter period of time because the method does not involve homologous recombination which has lower efficiency. Concretely, a recombinant virus resulting from insertion of a desired gene between the mutant FRT sequence and the wild-type FRT sequence can be obtained at a high frequency by firstly preparing adenovirus for gene transfer resulting from insertion of the mutant FRT sequence and the wild-type FRT sequence, thereafter infecting this virus with a cell appropriate for preparing recombinant adenovirus, such as 293 cell, and at the same time transferring plasmid DNA resulting from insertion of a desired gene between the wild-type FRT sequence and the mutant FRT sequence into the cell, and expressing FLP recombinase. In this case, it is desired that the adenovirus for gene transfer is prepared such that a packaging signal flanked by the FRT sequences is removed by FLP-dependent recombination, so that a desired virus can be selectively obtained by adding and substituting a packaging signal as well as a desired gene from the plasmid DNA. FLP recombinase may be transferred in a form of plasmid DNA, or a cell may be previously transformed so as to express FLP recombinase.

Examples of transformed cells expressing FLP recombinase include those cells capable of constitutively expressing FLP recombinase or those cells capable of inducing expression of FLP recombinase under given conditions. Examples of the latter include cells capable of inducing expression of FLP recombinase in the presence or absence of a drug; and those capable of inducing expression of FLP recombinase by allowing recombinase to act on cells resulting from insertion of a recognition sequence for recombinase-stuffer DNA-a recognition sequence for recombinase between its promoter and FLP gene.

Examples of recombinase and a recognition sequence thereof include Cre recombinase derived from P1 phage and loxP sequence. The method for allowing recombinase to act on a cell includes a method for gene transfer using plasmid DNA, liposome or the like; or a method for introducing a recombinase protein per se; and a method using a viral vector such as adenovirus vector. The method using adenovirus vector is desirable.

An embodiment where a recombinant adenovirus resulting from replacement of a foreign gene A with a foreign gene B is prepared will be described. An example of the structure of the recombinant adenovirus for gene transfer includes adenovirus resulting from insertion of FRT sequences in the order of adenovirus left inverted terminal repeat (ITR), a wild-type FRT sequence, a packaging signal, a wild-type FRT sequence, a gene A and a mutant FRT sequence. Here, a DNA fragment of the wild-type FRT sequence/the gene A is inserted into an E1-deletion site.

An example of plasmid DNA for inserting a foreign gene B includes a plasmid having a structure of a wild-type FRT sequence, a packaging signal, a gene B and a mutant FRT sequence. When the adenovirus for gene transfer and the plasmid DNA for inserting foreign gene B are simultaneously or sequentially transferred into a cell such as 293 cell so as to express FLP recombinase, the packaging signal flanked by the two wild-type FRT sequences in the adenovirus for gene transfer is removed, and a recombinant adenovirus resulting from replacement of a portion of a wild-type FRT sequence, a gene A and a mutant FRT sequence of the adenovirus with [wild-type FRT sequence/packaging signal/gene B/mutant FRT sequence] derived from the plasmid is generated. Since the packaging signal is removed by usual "excision reaction" between the two wild-type FRT sequences having high reaction efficiencies, from the adenovirus for transfer gene in which no gene substitution takes place, its viral DNA per se replicates, but the viral DNA is not packaged in virions and the adenovirus does not replicate as virus. On the other hand, since gene-replaced adenovirus carries a packaging signal, and can replicate as virus, the recombinant adenovirus resulting from replacement with "gene B" is obtained at a high frequency.

The insertion position of the mutant FRT sequence of the adenovirus for gene transfer may be at a flanking site of a foreign gene A, or a site apart from the gene A on the adenovirus genome. Examples of the insertion position of the latter include the non-translation region between L3 gene and E2A gene, E3 gene-deletion site, a portion between the upstream region of E4 gene and the right ITR, and the like. When the mutant FRT sequence is inserted at any of these positions to perform gene replacement, the size of the DNA between the wild-type FRT sequence and mutant FRT sequence of the plasmid for inserting a desired gene needs to be adjusted so that the generated adenovirus DNA is efficiently packaged in virions. It can be thought, however, that since the gene-replaced recombinant adenovirus is deficient of a gene essential for virus replication, when the recombinant adenovirus is used as a vector for gene therapy, side effects which have been problematic in the present adenovirus vector can be alleviated.

The above-mentioned method will be more concretely described in further detail. First, cells expressing adenovirus EIA gene suitable for the proliferation of replication-deficient adenovirus resulting in deletion of E1 gene, such as 293 cells, are transformed with DNA having a structure of [promoter/loxP sequence/drug-resistance gene/poly(A) sequence, loxP sequence/FLP gene/poly(A) sequence], to give cell lines expressing FLP in a Cre recombinase-dependent manner (Cre-dependent FLP expressing cell). Here, the drug-resistance gene is required for screening of transformed cell lines, and examples thereof include neomycin-resistance gene, hygromycin-resistant gene and the like. In addition, the promoter is not particularly limited as long as it functions in mammal cells and examples thereof include CAG promoter (Japanese Patent Laid-Open No. Hei 3-168087), EF-1α promoter [Gene, 91, 217–223 (1991)], SRα promoter [Molecular and Cellular Biology, 8, 466–472 (1991)], and the like. Further, a nuclear localization signal sequence may be ligated to the 3'-end or 5'-end of recombinase FLP gene.

The recombinant adenovirus for gene transfer also serve as a function of expressing FLP by feeding Cre recombinase to Cre-dependent FLP-expressing cells. The recombinant adenovirus for gene transfer has insertion of wild-type FRT sequence between a left ITR and a packaging signal; insertion of a wild-type FRT sequence and a Cre recombinase-expressing unit (containing a promoter and poly(A) sequence) in this order at its E1-deletion site; and insertion of a mutant FRT sequence to any of the non-translation region between L3 gene and E2A gene, E3 gene-deletion site, or a portion between the upstream region of E4 gene and a right ITR. In the following example, an embodiment in which a mutant FRT sequence is inserted between the upstream region of E4 gene and the right ITR will be described. The insertion site of the wild-type FRT sequence between the left ITR and the packaging signal is not particularly limited, and it is preferable to insert at positions 143 to 148 of the nucleotide sequence for human adenovirus type-5. The promoter is not particularly limited, as long as the promoter functions in mammal cells, and examples thereof include the above-mentioned CAG promoter, EF-1α promoter, SRα promoter and the like. Further, it is preferable that a nuclear localization signal sequence is ligated to the 5'-end or 3'-end of Cre recombinase gene sequence. The reasons therefor are such that Cre recombinase synthesized in cytoplasm is required to be transported into the nucleus to act effectively on DNA having loxP sequence, which is a recognition sequence for Cre recombinase, and the nuclear localization signal sequence accelerates the transport [Daniel Kalderon et al., Cell 39, 499–509(1984)]. Cre gene having the nuclear localization signal sequence can be obtained from plasmid pSRNCre [Kanegae, Y. et al., Nucleic Acad Res., 23, 3816–3821 (1995)] or the like.

An example of the plasmid for inserting a foreign gene includes a plasmid having a structure of [wild-type FRT sequence/packaging signal/expression unit of gene B/mutant FRT sequence]. Here, the DNA sequence between the wild-type FRT sequence and the packaging signal is not particularly limited. It is preferable to carry a DNA sequence which is identical to the recombinant adenovirus for gene transfer.

When the above-mentioned Cre-dependent FLP-expressing cells are infected with a recombinant adenovirus for gene transfer and transformed with plasmid for inserting a foreign gene, first, the drug resistance gene and poly(A) sequence between the two loxP sequences in the Cre-dependent FLP-expressing cells are removed by Cre protein expressed by the recombinant adenovirus for gene transfer, thereby expressing FLP recombinase. Next, the packaging signal flanked by the two wild-type FRT sequences in the Cre-expressing recombinant adenovirus for gene transfer is removed by the action of FLP recombinase, and the Cre-expression unit and the major portion of the adenovirus genome (L1 gene to L5 gene) between the wild-type FRT sequence and the mutant FRT sequence in the adenovirus for gene transfer are replaced with the [wild-type FRT sequence/packaging signal/expression unit of gene B/mutant FRT sequence] in a plasmid for inserting a foreign gene. Therefore, the adenovirus generated by gene replacement has a structure of [left ITR/FRT sequence/packaging signal/expression unit of gene B/mutant FRT/right ITR], which is deficient in a major portion of adenovirus genome, so that the adenovirus cannot be proliferated by this virus alone. On the other hand, since the packaging signal is removed from the recombinant adenovirus for gene transfer in which no gene replacement takes place, its genomic DNA replicates to produce proteins essential for the proliferation of the adenovirus; however, its genome per se is not be packaged in infectious virions, so that the virus per se does not proliferate but acts as helper virus. As a result, in the adenovirus generated by gene replacement, its genomic DNA replicates by adenovirus protein produced by this helper virus, and the adenovirus selectively proliferates as virus packaged in infectious virions because the adenovirus carries a normal packaging signal. Therefore, it is expected that a majority of the recombinant adenovirus generated by the series of reactions is the desired adenovirus in which a gene replacement has occurred and in which a majority of the adenovirus genome is deleted.

Further, there is provided a specific DNA recombination method, comprising carrying out a specific DNA recombination reaction in the presence of recombinase FLP, by using two mutant FRT sequences (SEQ ID NO: 32), each resulting from substitution of G with C at the 7th nucleotide of the spacer region in the following wild type FRT sequence (SEQ ID NO:1) derived from yeast 2μ DNA:

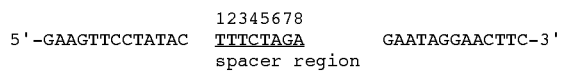

```
              12345678
5'-GAAGTTCCTATAC TTTCTAGA     GAATAGGAACTTC-3'
              spacer region
```

The DNA comprising a mutant FRT sequence of the present invention can be used for gene therapy as pharmaceuticals. Since the pharmaceutical of the present invention comprises the DNA of the present invention, it has an excellent property in that genes can be efficiently inserted into and removed from chromosome. Applications of the pharmaceutical of the present invention to gene therapy will be described below.

First, a mutant FRT sequence and a wild-type FRT sequence are previously inserted into chromosome of human cells. Therefore, the DNA having the mutant FRT sequence and the wild-type FRT sequence is used as a pharmaceutical.

The DNA may be administered in a form containing the DNA within viral vectors such as retrovirus or adeno-associated virus (AAV). Among them, in gene transfer by retrovirus, genes are randomly inserted in a chromosome. Therefore, AAV is preferably used, in the view point where there is a high probability that the genes are inserted at a particular site in a chromosome (AAV-S1 region on 19th chromosome) by AAV. Although a viral gene (Rep) encoded by AAV is essential for this site-specific gene transfer in a chromosome, a presently used AAV vector lacks in the specific incorporation mechanism into chromosome because a majority of the AAV gene is removed from these vectors. However, since the combined length of the mutant FRT sequence and the wild-type FRT sequence is as short as 100 bp or less, viruses resulting from insertion of two FRT sequences with having a whole viral gene of AAV can be prepared. It is desired that its insertion position is just inside of each of the inverted terminal repeats (ITRs) located at the both ends of AAV gene. The AAV resulting from insertion of the two FRT sequences is administered to human, whereby the two FRT sequences can be inserted into the chromosome.

Next, a pharmaceutical comprising a circular DNA resulting from insertion of a desired gene between the wild-type FRT sequence and the mutant FRT sequence, and recombinase FLP protein or DNA encoding FLP gene are administered to a subject, thereby removing the AAV gene flanked by two FRT sequences existing in a chromosome, to be replaced with the desired gene.

The pharmaceutical of the present invention may properly comprise any component for keeping an effective ingredient DNA molecule in a stable state, for instance, buffer component, degradation-protecting agent (for instance, nuclease inhibitor or the like). In addition, the pharmaceutical of the present invention may further comprise any drug suitable for introduction into a cell and/or a tissue.

The method for introducing a circular DNA molecule as a pharmaceutical and FLP recombinase or DNA molecule encoding FLP gene into a human cell includes a method using a known vector which has been used in gene therapy such as a viral vector or liposome vector.

When the pharmaceutical of the present invention is used in gene therapy, a method of administration to a patient includes in vivo method comprising directly introducing the pharmaceutical into the body, or ex vivo method comprising collecting a certain kind of cells from a human, transferring DNA into the collected cells extracorporeally, and reintroducing the gene-incorporated cells into the body [*Nikkei Science*, April, 1994, 20–54, *Gekkan Yakuji*, 36(1), 23–48, 1994, *Experimental Medicine, Separate Volume*, 12(15), 1994, *Nihon Idenshi Chiryogakkai Hen Idenshi Chiryo Kaihatsu Kenkyu Handobukku* (Japan Gene Therapy Association, eds., Gene Therapy Development and Research Handbook), NTS, 1999].

In the case of administration by in vivo method, the pharmaceutical of the present invention can be administered intravenously, intraarterially, subcutaneously, intracutaneously or intramuscularly, or administered directly to the subject tissue.

Concretely, for instance, detailed descriptions of the method for preparation of vectors and the administration method have been given in experimental guidebooks (*Experimental Medicine, Separate Volume, Standard Techniques of Gene Therapy*, Yodosha, 1996; *Experimental Medicine, Separate Volume, Gene Transfer & Expression Assay*, Yodosha, 1997; Japan Gene Therapy Association eds., *Gene Therapy Development and Research Handbook*, NTS, 1999).

In the human cells resulting from insertion of a gene in its chromosome, the mutant FRT sequence and the wild-type FRT sequence exist on both sides of the desired gene, and only ITR of AAV, not the structural gene of AAV, exists on the outside thereof. Therefore, expression of the desired gene can be expected to persist stably for a long period of time without expressing AAV-derived protein and serving as an antigen. Also, when the inserted gene is no longer necessary, a circular DNA molecule in which no gene exists between the wild-type FRT sequence and the mutant FRT sequence is administered, whereby the inserted gene can be removed from the chromosome. Further, when the insertion of a gene into the chromosome is again necessary, since the two FRT sequences still remain on a chromosome, a given gene can be inserted by the method described above. As described above, the DNA having mutant FRT sequence of the present invention can be used as a pharmaceutical in gene therapy by which a desired gene can be freely inserted in and removed from chromosome.

Alternatively, the range of application of the method for gene replacement can be broadened by using three or more FRT sequences of which substrate specificity is different from each other. The combination of three FRT sequences each having different substrate specificity from each other include, for instance, the combination of one wild-type FRT sequence and two mutant FRT sequences; the combination of three mutant FRT sequences; and the like. This method will be described by taking one example in which three different FRT sequences of a wild-type FRT sequence, a mutant FRT sequence 1 and mutant FRT sequence 2 exist in the same DNA. When DNA (a) having a wild-type FRT sequence, a gene A, a mutant FRT sequence 1, a gene B and a mutant FRT sequence 2, in this order, is allowed to react with a circular DNA (b) having a wild-type FRT sequence, a gene C and a mutant FRT sequence 1, in the presence of FLP recombinase, the gene A in DNA (a) is replaced with the gene C. Alternatively, when the DNA (a) is allowed to react with, instead of the circular DNA (b), a circular DNA (c) having a mutant FRT sequence 1, a gene D and a mutant FRT sequence 2, in this order, in the presence of FLP recombinase, the gene B in DNA (a) can be replaced with the gene D. In other words, only the target gene can be replaced with a given gene among a plurality of genes existing on the DNA (a) by using different circular DNAs.

The present invention will be hereinafter described in more detail in reference to the following examples. It should be noted, however, that the present invention is not limited to these examples and that other modifications can be made in the technical field of the present invention. Unless otherwise specified, various manipulations for handling phages, plasmids, DNAs, various kinds of enzymes, *Escherichia coli*, culture cells and others were carried out according to the methods described in *Molecular Cloning, A Laboratory Manual*, edited by T. Maniatis et al., 2nd ed., (1989), Cold Spring Harbor Laboratory.

EXAMPLE 1

<Preparation of Cell Extract Containing FLP Recombinase>

(1) Construction of Recombinant Adenovirus for Expressing FLP Recombinase

In order to obtain a plasmid in which the nucleotide sequences around the translation initiation codon of FLP recombinase were in accordance with Kozak sequence, the following procedures were performed.

(a) Plasmid pUCFLP is a plasmid resulting from insertion of a DNA fragment (1457 bp) containing a full-length FLP gene from SphI site (at position 5568) to XbaI site (at position 703) of 2μ DNA [6318 bp; James et al., Nature, 286, 860–865 (1980)] derived from yeast Saccharomyces cerevisiae into between SphI and XbaI sites on plasmid pUC19. The pUCFLP was digested with XbaI and SphI to obtain a fragment of about 1.5 kb containing a full-length FLP gene.

(b) A synthetic DNA adapter having the following sequences:

```
5'-AG CTT CTG CAG CAG ACC GTG CAT CAT G-3'   (SEQ ID NO: 10)
    3'-A GAC GTC GTC TGG CAC GTA-5'           (SEQ ID NO: 11)
``` wherein 5'-cohesive end can be ligated to HindIII-cleavage site, the other end can be ligated to SphI-cleavage site, wherein the adapter has PstI-site in the upstream region of its translation initiation codon was synthesized.

Both of DNAs (a) and (b) were inserted between HindIII and XbaI sites of pUC19 to give plasmid pUKFLP (4.1 kb).

A 1.4 kb fragment containing the FPL coding region resulting from digestion of pUKFLP with PstI and EspI and then blunt-ending was inserted at SwaI site between promoter and poly(A) sequence on cosmid vector pAxCAwt, to give cosmid vector pAxCAFLP.

293 cells were transformed with pAxCAFLP and adenovirus DNA-terminal protein complex by calcium phosphate co-precipitation method according to a known method [Miyake et al., Proc. Natl. Acad. Sci. 93, 1320–1324 (1996) and Japanese Patent Laid-Open No. Hei 7-298877], to give desired recombinant adenovirus expressing FLP, AxCAFLP (E1 and E3 gene deletions).

(2) Preparation of Cell Extract Containing FLP Recombinase

The following procedures were performed for the purpose of obtaining a cell extract containing FLP to be used for FLP recombinase-dependent recombination. 293 cells (cell line derived from human embryo kidney) in a 225 cm² flask were infected with AxCAFLP (about 1×10⁹ PFU) at 37° C. for 1 hour. A culture medium (5% FCS-containing DMEM medium) was added thereto, and the cells were cultured for additional 24 hours. After the cultivation, the resulting culture medium was centrifuged at 1000 rpm for 5 minutes with a low-speed centrifuge. Thereafter, the resulting supernatant was discarded to harvest cells. One milliliter of stock buffer [10% glycerol/20 mM Tris-HCl (pH 7.5)/300 mM sodium chloride/1 mM EDTA (pH 7.5)] was added to the cells to suspend the cells therein. The cells were disrupted in a sealed type sonicator at 200 W for 3 minutes (30 seconds× 6) to allow to release FLP recombinase existing in the cells. The resulting cell disruption fluid was then centrifuged with a high-speed centrifuge at 10000 rpm for 20 minutes. To the resulting supernatant, PMSF (phenylmethylsulfonyl fluoride) was added, so as to have a final concentration of 0.1 mM, and the resulting mixture was then froze and stored at −80° C.

EXAMPLE 2

<Preparation of Substrate DNA Containing Mutant FRT Sequence>

(1) Preparation of Synthetic DNA Containing Mutant FRT Sequence

There was prepared a synthetic DNA of 52 bp containing a mutant FRT sequence resulting from substitution of the 8-bp spacer region in a wild-type FRT sequence with other nucleotides. At the same time, a synthetic DNA of 52 bp containing a wild-type FRT sequence was also prepared. The structure of the synthetic DNA for wild-type FRT sequence is shown in FIG. 1, wherein sense strand is SEQ ID NO: 12, and anti-sense strand is SEQ ID NO: 13, and the sequences of nine kinds of synthetic DNAs each containing mutant FRT sequence (sense strand and anti-sense strand) and the sequence of the synthetic DNA for wild-type FRT sequence are shown in FIG. 2.

The sense strand and the anti-sense strand of the wild-type FRT sequence were not completely complementary to each other, so that they were designed such that each strand was annealed to form a double-stranded DNA, the resulting double-stranded DNA had 4-bp are over-hanged at the 5'-end of each strand, and that each end forms a digested fragment with restriction enzymes XhoI and SpeI, respectively. Therefore, in these double-stranded DNAs, an XhoI-fragment side is capable of binding to XhoI-digested fragment and SalI-digested fragment, and an SpeI-fragment side is capable of binding to SpeI-digested fragment and NheI-digested fragment.

All the single-stranded synthetic DNAs were phosphary-lated with T4 polynucleotide kinase at their 5'-end, and the sense strands and the anti-sense strands corresponding to the respective mutations were annealed. These double-stranded synthetic DNAs will hereinafter be referred to as mutant FRT synthetic DNAs.

(2) Preparation of Substrate DNA Containing Two Wild-type FRT Sequences or Two Mutant FRT Sequences Each Having Identical Sequences For the purpose of obtaining a substrate DNA having mutant FRT sequences each having an identical sequence in both ends of a linear DNA, the following procedures were performed:

Plasmid pBR322 was co-digested with restriction enzymes NheI and SalI, and each of a wild-type FRT synthetic DNA or 9 kinds of mutant FRT synthetic DNAs were subjected to ligation reaction (the molar ratio of plasmid: synthetic DNA being 1:20). Thereafter, the ligated product was then co-digested with restriction enzymes XhoI and SpeI. By the digestion of the ligated product with the restriction enzymes, the wild-type or mutant FRT synthetic DNAs which were bounded in plurality to both ends of pBR322 DNA was removed, so that a linear DNA of about 4.1 kb in which two wild-type FRT synthetic DNA sequences or two mutant FRT synthetic DNAs having an identical sequence to each other were respectively bounded with one by one in each other to both ends of pBR322 DNA. Next, these reaction products were subjected to electrophoresis on agarose gel, and a DNA band of about 4.1 kb was cut out from the gel and then purified by using GEAN-CLEAN II (manufactured by BIO101). According to the procedures, there were obtained linear DNA fragments in which two wild-type FRT sequences or two mutant FRT sequences each having an identical sequence to each other were respectively bounded to both ends of pBR322 DNA.

In order to construct a plasmid in which a DNA fragment derived from adenovirus type-5 was bounded to this fragment, the following procedures were carried out.

Cosmid vector pAxcw (Japanese Patent Laid-Open No. Hei 8-308585, p. 15) resulting from insertion of an almost full-length adenovirus type-5 gene other than E1 and E3 genes was co-digested with restriction enzymes XbaI and XhoI, and a 3.8 kb fragment (at positions 24,796th–28,592nd in adenovirus type-5 nucleotide sequence) was isolated from the resulting DNA fragments. When this 3.8 kb fragment was ligated to a DNA fragment in which FRT synthetic DNA sequences having an identical sequence to each other were respectively bounded to both ends of pBR322 DNA mentioned above by using ligase, restriction enzyme SpeI fragment and XbaI-fragment were bound to each other, and consequently circularized. *Escherichia coli* was transformed with this DNA, to give plasmid pBxxAxx (7.9 kb, FIG. 3) having two wild-type FRT sequences or two mutant FRT sequences having an identical sequence to each other. The pBxxAxx is a collective term for a plasmid having two FRT sequences each having an identical sequence to each other. For instance, when the FRT sequences are wild-type FRT, the corresponding plasmid is referred to as pBfwtAfwt; when the FRT sequences are F3, the corresponding plasmid is referred to as pBF3AF3; and when the FRT sequences are f2161, the corresponding plasmid is referred to as pBf2161Af2161.

pBfwtAfwt and 9 kinds of plasmids each containing mutant FRT sequences were digested with a restriction enzyme DraI and the resulting fragments obtained were used as substrate DNA for FLP-dependent DNA recombination as described below.

EXAMPLE 3

<FLP-Dependent DNA Recombination Reaction Between Two Mutant FRT Sequences Each Having the Identical Sequence to Each Other>

Whether or not FLP-dependent recombination reaction caused between the two mutant FRT sequences was studied by the assay described below. The DraI-digested plasmid DNA (1.5 µg) prepared in Example 2 and the cell extract containing FLP (25 µl) prepared in Example 1 were added to buffer containing 50 mM Tris-HCl (pH 7.5)/10 mM MgCl$_2$/5 mM DTT in its final concentration (the volume of reaction solution: 50 µl), and the reaction mixture was incubated at 30° C. for 30 minutes. After the termination of the reaction, 200 µl of sterilized water and 50 µl of 20 mM EDTA solution (pH 8.0) were added to the reaction mixture. The reaction mixture was extracted with phenol/chloroform and with chloroform. The resulting product was precipitated with ethanol, to obtain DNA. The resulting DNA was then solubilized in 20 µl of TE buffer (pH 8.0) containing RNaseA (20 µg/ml). Next, an entire volume of the resultant was digested with restriction enzyme NcoI, and subjected to electrophoresis on agarose gel. Thereafter, DNA bands detected by ethidium bromide (EtBr) staining were analyzed.

Since a restriction enzyme NcoI site exists in the substrate DNA at only one site, when the DraI-digested substrate DNA (7.2 kb and 0.7 kb) without causing FLP-dependent recombination reaction is digested with restriction enzyme NcoI, three bands, 5.9 kb, 1.3 kb as well as 0.7 kb bands, are generated. On the other hand, when the substrate DNA causes FLP-dependent recombination reaction, a circular DNA of about 3.8 kb having one mutant FRT and a linear DNA of about 3.4 kb having one mutant FRT is generated. Therefore, when these DNAs are digested with restriction enzyme NcoI, three bands, including the above-mentioned 3.8 kb and 3.4 kb bands as well as 0.7 kb band, are generated (see FIG. 4). Therefore, since 3.8 kb and 3.4 kb bands indicate that the FLP-dependent recombination reaction took place, and 5.9 kb and 1.3 kb bands indicate that the recombination reaction did not take place, the efficiency of the recombination is found by the ratio in the amounts of these bands.

In order to numerically express the reaction efficiency, the ratio of the amount of a whole DNA of the reaction system to the sum of amount of DNA at 3.8 kb and 3.4 kb bands was calculated as the recombination ratio (%) between the two FRT sequences.

According to the present determination method, the recombination ratio between two wild-type FRT sequences was 4.8%, and the recombination ratio between the prior art mutant sequences F3 was 3.1%, which was obviously lower than that for the wild-type FRT sequences. In contrast, the recombination ratio for f2161 was 4.5%, and the recombination ratio for f2262 was 3.8%, both showing higher recombination ratio than that for F3. Further, the recombination ratio for f2151 was 2.9%, and the recombination ratio for f61 was 2.6%, which were slightly lower than that for F3, and each of recombination ratio for f2272 and f2273 was 0. Further, the recombination ratio of a known sequence f72 was 10.9%, which was twice or higher than that for the wild-type FRT sequence.

It was shown from the above results that the mutant FRT sequences f2161 and f2262 of the present invention was excellent in the recombination efficiency, and those of f2151 and f61 had almost the same level of recombination efficiency as compared to that for the mutant FRT sequence F3.

EXAMPLE 4

<FLP-Dependent DNA Recombination Between Wild-Type FRT Sequence and Mutant FRT Sequence>

(1) Construction of Plasmid (pBRFRT) Containing One Wild-Type FRT Sequence

In order to construct a plasmid (pBRFRT) resulting from insertion of one wild-type FRT sequence into plasmid pBR322, the procedures of the following (a) and (b) were performed:

(a) Plasmid pBRwt [Lee, G. et al., *Gene* 14, 55–65 (1998)], resulting from replacement of a 0.4 kb fragment between the NheI site and the EcoNI site of plasmid pBR322 with a DNA containing a wild-type loxP sequence using XhoI linker, is digested with restriction enzyme XhoI. The resulting fragments are ligated to a synthetic DNA of 52 bp containing a wild-type FRT sequence prepared in item (1) of Example 2. Thereafter, the ligated product is co-digested with restriction enzymes SpeI and PstI, to remove the wild-type FRT synthetic sequences which are bound in plurality to both ends of pBR322 DNA. Next, the reaction mixture is subjected to electrophoresis on agarose gel, and a DNA band of about 3 kb is cut out from the gel, to give a fragment of about 3.0 kb containing one wild-type FRT sequence.

(b) Plasmid pBR322 is co-digested with restriction enzymes PstI and NheI, and the resulting fragments are subjected to electrophoresis on agarose gel. Of two DNA bands generated, a fragment of about 1.0 kb is collected.

Figure 5:
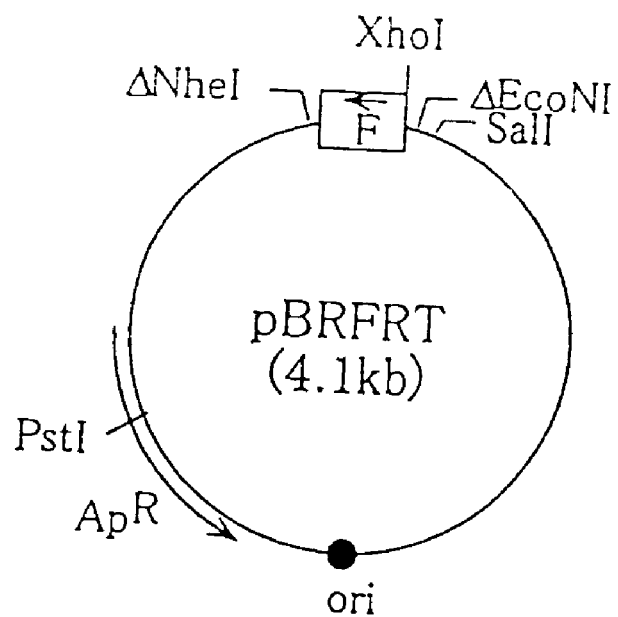
FIG. 5 is a schematic view showing the structure of plasmid pBRFRT, wherein "F" means a wild-type FRT sequence, the arrow above the character indicates the orientation of the FRT sequence, $Ap^R$ is an ampicillin-resistant gene, and ori is a replication origin of *Escherichia coli*.

Both the DNAs prepared in items (a) and (b) are ligated to each other, to give plasmid pBRFRT (4.4 kb, FIG. 5) resulting from insertion of one wild-type FRT sequence between the NheI site and the EcoNI site of the pBR322.

(2) Construction of Plasmid Containing Wild-Type FRT Sequence and Mutant FRT Sequence, and Preparation of Substrate DNA Since SalI site is located at a position about 30 bp apart from the wild-type FRT sequence on plasmid pBRFRT, the pBRFRT is digested with restriction enzyme SalI to be linearized, and each of the synthetic DNAs (9 kinds) of 52 bp containing the mutant FRT sequence prepared in item (1) of Example 2 is ligated. By these manipulations, the XhoI-digested fragment side of each mutant FRT synthetic DNA is bound to the SalI-digested site on pBRFRT. Next, the reaction mixture is subjected to co-digestion with restriction enzymes SpeII and XhoI, to remove the mutant FRT synthetic DNAs bound in plurality to both ends of pBRFRT. Thereafter, unreacted and restriction enzyme-digested mutant FRT synthetic DNAs are removed from the reaction mixture by using GEANCLEAN II (manufactured by BIO101), to give a linear DNA (about 4.1 kb) in which one wild-type FRT sequence is bounded to one end and in which one mutant FRT sequence is bounded to the other end.

This fragment and an about 3.8 kb fragment prepared in item (2) of Example 2 resulting from co-digestion of adenovirus type-5 genome with restriction enzymes XhoI and XbaI are ligated, to give plasmid pBfwtAxx (7.9 kb, FIG. 6). Here, the plasmid pBfwtAxx is a collective term for a series of plasmids constructed by the above-mentioned method, which actually refers to those plasmids each having one mutant FRT sequence and one wild-type FRT sequence shown in FIG. 2.

Plasmid pBfwtAxx is digested with restriction enzyme DraI to be used as a substrate DNA in FLP-dependent DNA recombination reaction as described below.

(3) FLP-Dependent DNA Recombination Reaction Between Wild-Type FRT Sequence and Mutant FRT Sequence The above-mentioned substrate DNA is added to the reaction solution given in Example 3 above, and the FLP-dependent recombination reaction is performed at 30° C. for 30 minutes. After the termination of the reaction, DNA is purified, digested with restriction enzyme NcoI, and subjected to electrophoresis on agarose gel. DNA bands detected by EtBr staining is analyzed.

Since only one restriction enzyme NcoI-site exists in the substrate DNA, when DraI-digested substrate DNA (7.2 kb and 0.7 kb) without causing FLP-dependent recombination reaction is digested with restriction enzyme NcoI, three bands of 5.9 kb fragment, 1.3 kb fragment as well as 0.7 kb fragment are generated. On the other hand, when substrate DNA causes FLP-dependent recombination reaction, a circular DNA of about 3.8 kb having one FRT sequence and a linear DNA of about 3.4 kb having one FRT sequence are generated. Thereafter, when these DNAs are digested with restriction enzyme NcoI, three bands of 3.8 kb, 3.4 kb as well as 0.7 kb fragments are generated (see FIG. 7). Therefore, since 3.8 kb and 3.4 kb bands indicate that the FLP-dependent recombination reaction took place, and 5.9 kb and 1.3 kb bands indicate that the FLP-dependent recombination reaction did not take place, the recombination efficiency is found by the ratio of the amount of these bands.

EXAMPLE 5

<FLP-Dependent DNA Recombination Reaction Between Wild-Type FRT Sequence and Mutant FRT Sequence>

(1) Construction of Plasmid Containing Wild-Type FRT Sequence and Mutant FRT Sequence, and Preparation of Substrate DNA Synthetic DNA of 54 bp (SEQ ID NO: 33) containing 34 bp wild-type FRT sequence and its complementary strand were inserted into SmaI site on plasmid pUC18, to give plasmid pUFwF (2.8 kb, "A" in FIG. 8) resulting in insertion of two wild-type FRT sequences in the same orientation, and having the SwaI site between the two wild-FRT sequences.

Plasmid pCALNLZ [Y. Kanegae et. al., Gene, 181, 207–212 (1996)] was digested with MluI and XhoI and the fragments were then blunt-ended, to give a fragment containing neomycin-resistance gene and SV40 poly(A) sequence. Next, the fragment containing neomycin-resistance gene and SV40 poly(A) sequence was inserted into the SwaI site on pUFwF, to give plasmid pUFNF (3.9 kb, "B" in FIG. 8).

Figure 8:
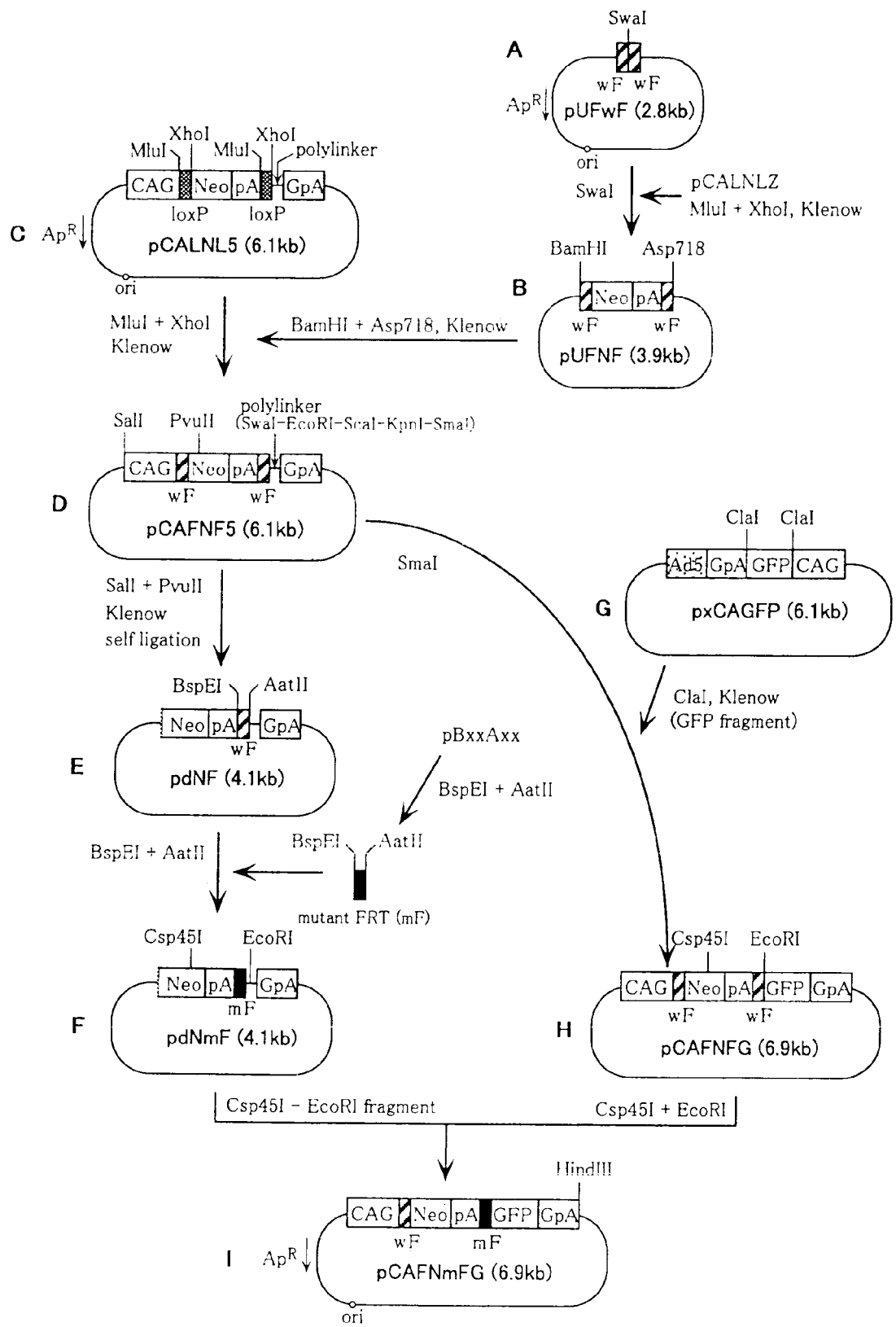
FIG. 8 is a schematic view showing a method for constructing plasmid pCAFNmFG, wherein wF is a wild-type FRT sequence, and mF is a mutant FRT sequence, wherein CAG is CAG promoter, GpA is globin poly (A) sequence, pA is poly(A) sequence of SV40, and Ad5 is a portion of human adenovirus type-5 genome.

A synthetic poly-linker of 27 bp (5'-AAA TTG AAT TCG AGC TCG GTA CCC GGG-3', SEQ ID NO: 34) and its complementary strand were inserted into the SwaI site on plasmid pCALNLw [Kanegae Y. et al., Gene, 181, 207–212 (1996)], to give plasmid pCALNL5 (6.1 kb, "C" in FIG. 8). Next, pUFNF was digested with BamHI and Asp718, and the resulting fragments were then blunt-ended, to give a fragment of about 1.2 kb containing FRT sequence/neomycin-resistance gene/SV40 poly(A) sequence/FRT sequence. The above-mentioned 1.2 kb fragment and an about 4.9 kb fragment containing CAG promoter, resulting from digestion of pCALNL5 with MluI and XhoI followed by blunt-ending were ligated, to give plasmid pCAFNF5 (6.1 kb, "D" in FIG. 8). The pCAFNF5 contains a poly-linker for cDNA insertion (SwaI-EcoRI-ScaI-KpnI-SmaI site) between the wild-type FRT sequence and globin poly(A) sequence.

Plasmid pCAFNF5 was digested with SalI and PvuII, and the fragments were then blunt-ended. Thereafter, the resulting fragments were subjected to self ligation, to give plasmid pdNF (4.1 kb, "E" in FIG. 8) resulting from removal of [promoter-wild-type FRT sequence-a part of neomycin-resistance gene].

The plasmid pBxxAxx (xx is either f72, f2161, f2262 or F3) having two mutant FRT sequences having an identical sequence to each other prepared in Example 2 was co-digested with BspEI and AatII, to give a 50 bp fragment (a) having a mutant FRT sequence. On the other hand, plasmid pdNF was co-digested with BspEI and AatII, to give a fragment (b) not containing wild-type FRT sequence. Both of the fragments (a) and (b) were ligated, to give plasmid pdNmF (4.1 kb, "F" in FIG. 8) resulting from substitution of the wild-type FRT sequence of pdNF with a mutant FRT sequence.

The expression plasmid pEGFP-C1 (4.7 kb, manufactured by CLONTECH) was inserted with DNA sequence encoding mutant green fluorescent protein (GFP). Thereafter, the following synthetic DNA linkers of 18 bp:

5'-GATCTTACTAGTAGGATC-3' (SEQ ID NO:35)

3'-AATGATCATCCTAGAGCT-5' (presented in the 5'-3' direction, SEQ ID NO:36), which were designed to have a BglII site at one end and an XhoI site at the other end as well as to contain continuous two stop codons in its sequence, were inserted between the BglII site and XhoI site in the multi-cloning site present between the 3'-end of GFP gene and poly(A) sequence on plasmid pEGFP-C1, to give plasmid pEGFP-s.

Plasmid pEGFP-s was co-digested with AgeI and XhoI, and the fragments were then blunt-ended at its both ends with Klenow enzyme, to give a DNA fragment (a) of about 0.8 kb containing a full-length GFP gene. In addition, in cosmid vector pAxCAwt [Kanegae, Y. et al., *Nucleic Acid Res.*, 23, 3816–3821 (1995)] containing a major part of adenovirus type-5 genome other than adenovirus E1 and E3 genes, to which CAG promoter was inserted at the E1 gene-deletion site, there exist cloning sites in the order of ClaI site-SwaI site-ClaI site between the promoter and poly(A) sequence. Therefore, pAxCAwt was digested with SwaI, and then ligated to the above-mentioned DNA fragment (a) of 0.8 kb, to give cosmid vector pAxCAGFP.

The pAxCAGFP was digested with SalI, and thereafter subjected to self-ligation, to give plasmid pxCAGFP (6.1 kb, "G" in FIG. 8) resulting from removal of a large part of adenovirus DNA (containing the left end of about 0.4 kb). In pxCAGFP, since ClaI sites exist at both ends of GFP gene, pxCAGFP was digested with ClaI, and the resulting fragment was then blunt-ended at both ends with Klenow enzyme, to give a DNA fragment of about 0.8 kb containing a full-length GFP gene. This fragment was inserted into the SmaI site on the poly-linker on the plasmid pCAFNF5 described above, to give plasmid pCAFNFG (6.8 kb, "H" in FIG. 8).

Finally, a portion of between Csp45I site and EcoRI site on plasmid pCAFNFG was substituted by a portion of between Csp45I site and EcoRI site on plasmid pdNmF, to give a finally desired plasmid pGAFNmFG (6.9 kb, "I" in FIG. 8). Plasmid pCAFNmFG is a collective term for a series of plasmids containing one each of the wild-type FRT sequence and the mutant FRT sequence. The above-mentioned pCAFNmFGS actually contain either one of mutant FRT sequences (mF) of f72, f2161, f2262 or F3.

These plasmids pCAFNmFGs or a plasmid pCAFNFG containing two wild-type FRT sequences were digested with restriction enzyme HindIII, to form linear DNAs which were then used as substrate DNA for FLP-dependent recombination.

(2) FLP-Dependent DNA Recombination Between Wild-Type FRT Sequence and Mutant FRT Sequence One microgram of the above-mentioned substrate DNA and 25 μl of cell extract containing FLP prepared in Example 1 were added to a buffer containing 50 mM Tris-HCl (pH 7.5)/10 mM $MgCl_2$/5 mM DTT in a final concentration (volume of reaction mixture: 50 μl), and the reaction mixture was incubated at 30° C. for 30 minutes. After the termination of the reaction, 200 μl of sterilized water and 50 μl of 20 mM EDTA solution (pH 8.0) were added to the reaction solution, and the reaction mixture was extracted with phenol/chloroform and with chloroform. The resulting product was precipitated with ethanol. The resulting DNA was solubilized in 20 μl of TE buffer (pH 8.0) containing RNaseA (20 μg/ml). Next, the entire volume of the resulting product was digested with restriction enzyme FspI, and the resulting fragment was subjected to electrophoresis on agarose gel. DNA bands detected by ethidium bromide (EtBr) staining were analyzed.

Figure 9:
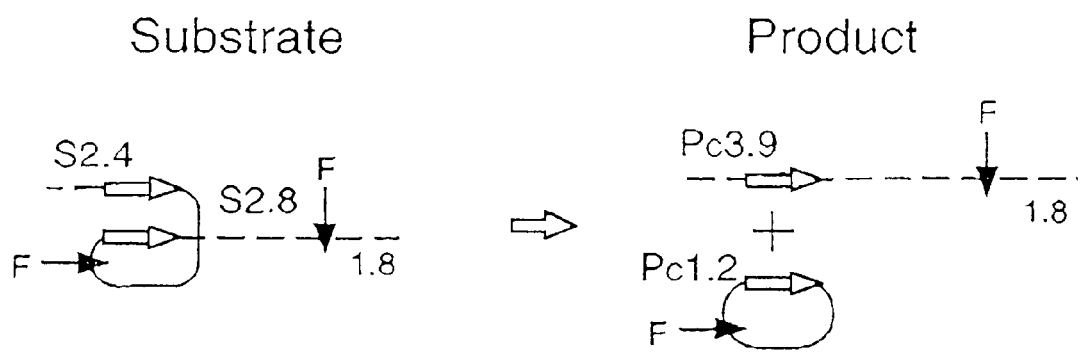
FIG. 9 is a schematic view showing the principle of FLP recombinase-dependent recombination reaction between the wild-type FRT sequence and the mutant FRT sequence, wherein open arrows indicate FRT sequences, and solid arrows indicate restriction enzyme FspI-sites, wherein the numerals indicate the lengths (kb) of FspI-digested DNA fragments.

In the HindIII-digested substrate DNA, there exist two restriction enzyme FspI sites. In the case where the FLP-dependent recombination reaction does not take place, when the substrate DNA is digested by restriction enzyme FspI, three bands of 2.8 kb, 2.4 kb, and 1.8 kb are generated. On the other hand, in the case where the FLP-dependent recombination reaction is caused by the substrate DNA, a linear DNA of about 5.7 kb and a circular DNA of about 1.2 kb are generated, so that when these DNAs are digested with restriction enzyme FspI, three bands of 3.9 kb, 1.2 kb and 1.8 kb are generated (FIG. 9). Therefore, since the bands of 3.9 kb and 1.2 kb indicate that the FLP-dependent recombination reaction took place, and 2.8 kb and 2.4 kb bands indicate that the FLP-dependent recombination reaction did not take place, the recombination efficiency is found by the ratio of the amount of these bands. Therefore, in order to numerically express the reaction efficiency, the ratio of the amount of 3.9 kb band to a whole DNA after reaction was calculated as the recombination ratio (unit: %) between two FRT sequences.

When the recombination ratio between two wild-type FRT sequences was obtained using the present determination method, the recombination ratio was about 28%. On the other hand, in the recombination ratio between the wild-type FRT sequence and the mutant FRT sequence, the determined recombination ratio for all the mutant FRT sequences (f2161, f2262, f72 and F3) was below the detection limit (below 0.2%).

It was clarified from the results of the present Example as well as Example 3 that the mutant FRT sequences f2161 and f2262 of the present invention causes the recombination efficiently between mutant FRT sequences having an identical sequence to each other, but causes no recombination reaction with the wild-type FRT sequence.

Sequence Free Text

SEQ ID NO: 10 is a sequence for synthesized DNA adaptor.

SEQ ID NO: 11 is a sequence for synthesized DNA adaptor.

SEQ ID NO: 12 is an oligonucleotide sequence designed based on wild-type FRT sequence.

SEQ ID NO: 13 is an oligonucleotide sequence designed based on wild-type FRT sequence.

SEQ ID NO: 14 is an oligonucleotide sequence designed based on mutant FRT sequence.

SEQ ID NO: 15 is an oligonucleotide sequence designed based on mutant FRT sequence.

SEQ ID NO: 16 is an oligonucleotide sequence designed based on mutant FRT sequence.

SEQ ID NO: 17 is an oligonucleotide sequence designed based on mutant FRT sequence.

SEQ ID NO: 18 is an oligonucleotide sequence designed based on mutant FRT sequence.

SEQ ID NO: 19 is an oligonucleotide sequence designed based on mutant FRT sequence.

SEQ ID NO: 20 is an oligonucleotide sequence designed based on mutant FRT sequence.

SEQ ID NO: 21 is an oligonucleotide sequence designed based on mutant FRT sequence.

SEQ ID NO: 22 is an oligonucleotide sequence designed based on mutant FRT sequence.

SEQ ID NO: 24 is an oligonucleotide sequence designed based on mutant FRT sequence.

SEQ ID NO: 25 is an oligonucleotide sequence designed based on mutant FRT sequence.

SEQ ID NO: 26 is an oligonucleotide sequence designed based on mutant FRT sequence.

SEQ ID NO: 27 is an oligonucleotide sequence designed based on mutant FRT sequence.

SEQ ID NO: 28 is an oligonucleotide sequence designed based on mutant FRT sequence.

SEQ ID NO: 29 is an oligonucleotide sequence designed based on mutant FRT sequence.

SEQ ID NO: 30 is an oligonucleotide sequence designed based on mutant FRT sequence.

SEQ ID NO: 31 is an oligonucleotide sequence designed based on mutant FRT sequence.

SEQ ID NO: 32 is an oligonucleotide sequence designed based on mutant FRT sequence.

SEQ ID NO: 33 is an oligonucleotide sequence designed based on FLP recognition sequence.

SEQ ID NO: 34 is an oligonucleotide sequence designed based on recognition sequences of SwaI, EcoRI, ScaI, KpnI and SmaI in this order.

SEQ ID NO: 35 is an oligonucleotide sequence designed based on sequence encoding BglII recognition sequence, two stop codons, and XhoI recognition sequence.

SEQ ID NO: 36 is an oligonucleotide sequence designed based on sequence encoding BglII recognition sequence, two stop codons, and XhoI recognition sequence.

INDUSTRIAL APPLICABILITY

The DNA comprising a mutant FRT sequence of the present invention exhibits excellent properties of causing recombination reaction between two mutant FRT sequences each having an identical sequence to each other in the presence of FLP recombinase but causing no recombination reaction with the wild-type FRT sequence. Therefore, there is exhibited an excellent effect that a highly efficient method for a gene replacement can be performed. Further, there is provided a highly efficient method for a gene replacement in higher eucaryote cell such as animal cells by combining a wild-type FRT sequence with a mutant FRT sequence, or combining mutant FRT sequences of different sequences using the DNA of the present invention.

---

The invention claimed is:

1. An isolated DNA encoding a mutant FRT sequence comprising the nucleotide sequence shown in any one of SEQ ID NOS: 2 to 5.

2. The isolated DNA according to claim 1, wherein said mutant FRT sequence possesses a property of causing no specific DNA recombination reaction with a second FRT sequence having a different sequence in the 8-bp spacer region in the presence of recombinase FLP.

3. An isolated DNA comprising at least one wild type FRT sequence comprising SEQ ID NO: 1 and at least one mutant FRT sequence of claim 1.

4. The isolated DNA according to claim 3, having a desired nucleotide sequence between the wild type FRT sequence and the mutant FRT sequence.

5. An isolated DNA comprising at least two mutant FRT sequences of claim 2, wherein the at least two mutant FRT sequences are different relative to one another in the 8-bp spacer region.

6. The isolated DNA according to claim 5, further comprising a desired nucleotide sequence between two of the at least two mutant FRT sequences.

7. An isolated or cultured cell which is transformed with the DNA of claim 3 in vitro.

8. A method for replacing a nucleotide sequence in vitro, comprising the steps of
reacting a first DNA comprising in sequential order a wild type FRT sequence comprising SEQ ID NO: 1, a first nucleotide sequence of interest and a mutant FRT sequence comprising any one of SEQ ID NOS: 2–5 with a second DNA comprising in sequential order a wild type FRT sequence comprising SEQ ID NO: 1, a second nucleotide sequence of interest which nucleotide sequence is different from that of the first nucleotide sequence of interest, and a mutant FRT sequence which is identical to the mutant FRT sequence of the first DNA in the presence of recombinase FLP,
thereby obtaining a DNA in which the first nucleotide sequence of interest is replaced by the second nucleotide sequence of interest in the first DNA.

9. A method for replacing a nucleotide sequence in vitro, comprising the steps of
reacting a first DNA comprising in sequential order a mutant FRT sequence of claim 2, a first nucleotide sequence of interest and a second mutant FRT sequence of claim 3, wherein the first and second mutant FRT sequences are different relative to one another in the 8-bp spacer region with a second DNA comprising in sequential order the first mutant FRT sequence, a second nucleotide sequence of interest which nucleotide sequence is different from that of the first nucleotide sequence of interest, and the second mutant FRT sequence in the presence of recombinase FLP,
thereby obtaining a DNA in which the first nucleotide sequence of interest is replaced by the second nucleotide sequence of interest in the first DNA.

10. The method according to claim 8, wherein said first DNA is a chromosomal DNA of a cell, and said second DNA is a plasmid DNA or a DNA of double-stranded circular DNA virus.

11. The method according to claim 8, wherein said first DNA is a chromosomal DNA of a cell.

12. The method according to claim 8, wherein said first DNA is a chromosomal DNA of a double-stranded DNA virus, and said second DNA is a plasmid DNA or a DNA of a double-stranded circular DNA virus.

13. The method according to claim 8, wherein said first DNA is a chromosomal DNA of a double-stranded DNA virus.

14. The method according to claim 12, wherein the double-stranded DNA virus is adenovirus.

15. The method according to claim 13, wherein the double-stranded DNA virus is adenovirus.

16. The method according to claim 9, wherein said first DNA is a chromosomal DNA of a cell, and said second DNA is a plasmid DNA or a DNA of a double-stranded circular DNA virus.

17. The method according to claim 9, wherein said first DNA is a chromosomal DNA of a cell.

18. The method according to claim 9, wherein said first DNA is a chromosomal DNA of a double-stranded DNA virus, and said second DNA is a plasmid DNA or a DNA of a double-stranded circular DNA virus.

19. The method according to claim 9, wherein said first DNA is a chromosomal DNA of a double-stranded DNA virus.

20. The method according to claim 18, wherein the double-stranded DNA virus is adenovirus.

21. The method according to claim 19, wherein the double-stranded DNA virus is adenovirus.

* * * * *

SEQUENCE LISTING

```
<160> NUMBER OF SEQ ID NOS: 36

<210> SEQ ID NO 1
<211> LENGTH: 34
<212> TYPE: DNA
<213> ORGANISM: Saccharomyces cerevisiae

<400> SEQUENCE: 1
gaagttccta tactttctag agaataggaa cttc                              34

<210> SEQ ID NO 2
<211> LENGTH: 34
<212> TYPE: DNA
<213> ORGANISM: Saccharomyces cerevisiae

<400> SEQUENCE: 2
gaagttccta tactctctgg agaataggaa cttc                              34

<210> SEQ ID NO 3
<211> LENGTH: 34
<212> TYPE: DNA
<213> ORGANISM: Saccharomyces cerevisiae

<400> SEQUENCE: 3
gaagttccta tactctccag agaataggaa cttc                              34

<210> SEQ ID NO 4
<211> LENGTH: 34
<212> TYPE: DNA
<213> ORGANISM: Saccharomyces cerevisiae

<400> SEQUENCE: 4
gaagttccta tactatcttg agaataggaa cttc                              34

<210> SEQ ID NO 5
<211> LENGTH: 34
<212> TYPE: DNA
<213> ORGANISM: Saccharomyces cerevisiae

<400> SEQUENCE: 5
```

```
gaagttccta tactttctgg agaataggaa cttc                                    34

<210> SEQ ID NO 6
<211> LENGTH: 34
<212> TYPE: DNA
<213> ORGANISM: Saccharomyces cerevisiae

<400> SEQUENCE: 6
gaagttccta tactatttga agaataggaa cttc                                    34

<210> SEQ ID NO 7
<211> LENGTH: 34
<212> TYPE: DNA
<213> ORGANISM: Saccharomyces cerevisiae

<400> SEQUENCE: 7
gaagttccta taccttgtga agaataggaa cttc                                    34

<210> SEQ ID NO 8
<211> LENGTH: 34
<212> TYPE: DNA
<213> ORGANISM: Saccharomyces cerevisiae

<400> SEQUENCE: 8
gaagttccta tactatctac agaataggaa cttc                                    34

<210> SEQ ID NO 9
<211> LENGTH: 34
<212> TYPE: DNA
<213> ORGANISM: Saccharomyces cerevisiae

<400> SEQUENCE: 9
gaagttccta tactgtctat agaataggaa cttc                                    34

<210> SEQ ID NO 10
<211> LENGTH: 27
<212> TYPE: DNA
<213> ORGANISM: Artificial Sequence
<220> FEATURE:
<223> OTHER INFORMATION: The oligonucleotide is synthesized DNA adaptor.

<400> SEQUENCE: 10
agcttctgca gcagaccgtg catcatg                                            27

<210> SEQ ID NO 11
<211> LENGTH: 19
<212> TYPE: DNA
<213> ORGANISM: Artificial Sequence
<220> FEATURE:
<223> OTHER INFORMATION: The oligonucleotide is synthesized DNA adaptor.

<400> SEQUENCE: 11
atgcacggtc tgctgcaga                                                     19

<210> SEQ ID NO 12
<211> LENGTH: 52
<212> TYPE: DNA
<213> ORGANISM: Artificial Sequence
<220> FEATURE:
<223> OTHER INFORMATION: Designed oligonucleotide based on wild type FRT
      sequence.

<400> SEQUENCE: 12
tcgaggacgt cgaagttcct atactttcta gagaatagga acttctccgg aa                52
```

<210> SEQ ID NO 13
<211> LENGTH: 52
<212> TYPE: DNA
<213> ORGANISM: Artificial Sequence
<220> FEATURE:
<223> OTHER INFORMATION: Designed oligonucleotide based on wild type FRT
      sequence.

<400> SEQUENCE: 13
ctagttccgg agaagttcct attctctaga aagtatagga acttcgacgt cc           52

<210> SEQ ID NO 14
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 14
tcgaggacgt cgaagttcct atactatcta gagaatagga acttctccgg aa           52

<210> SEQ ID NO 15
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 15
tcgaggacgt cgaagttcct atactttctg gagaatagga acttctccgg aa           52

<210> SEQ ID NO 16
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 16
tcgaggacgt cgaagttcct atactttcta cagaatagga acttctccgg aa           52

<210> SEQ ID NO 17
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 17
tcgaggacgt cgaagttcct atactatttg aagaatagga acttctccgg aa           52

<210> SEQ ID NO 18
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 18
tcgaggacgt cgaagttcct atactctctg gagaatagga acttctccgg aa           52

-continued

<210> SEQ ID NO 19
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 19
tcgaggacgt cgaagttcct atactatcta cagaatagga acttctccgg aa          52

<210> SEQ ID NO 20
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 20
tcgaggacgt cgaagttcct atactctcca gagaatagga acttctccgg aa          52

<210> SEQ ID NO 21
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 21
tcgaggacgt cgaagttcct atactatctt gagaatagga acttctccgg aa          52

<210> SEQ ID NO 22
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 22
tcgaggacgt cgaagttcct atactgtcta tagaatagga acttctccgg aa          52

<210> SEQ ID NO 23
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 23
ctagttccgg agaagttcct attctctaga tagtatagga acttcgacgt cc          52

<210> SEQ ID NO 24
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 24
ctagttccgg agaagttcct attctccaga aagtatagga acttcgacgt cc          52

```
<210> SEQ ID NO 25
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 25
ctagttccgg agaagttcct attctgtaga agtatagga acttcgacgt cc          52

<210> SEQ ID NO 26
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 26
ctagttccgg agaagttcct attcttcaaa tagtatagga acttcgacgt cc          52

<210> SEQ ID NO 27
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 27
ctagttccgg agaagttcct attctccaga gagtatagga acttcgacgt cc          52

<210> SEQ ID NO 28
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 28
ctagttccgg agaagttcct attctgtaga tagtatagga acttcgacgt cc          52

<210> SEQ ID NO 29
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 29
ctagttccgg agaagttcct attctctgga gagtatagga acttcgacgt cc          52

<210> SEQ ID NO 30
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 30
ctagttccgg agaagttcct attctcaaga tagtatagga acttcgacgt cc          52

<210> SEQ ID NO 31
```

```
<211> LENGTH: 52
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 31
ctagttccgg agaagttcct attctataga cagtatagga acttcgacgt cc           52

<210> SEQ ID NO 32
<211> LENGTH: 34
<212> TYPE: DNA
<213> ORGANISM: Artificial Sequence
<220> FEATURE:
<223> OTHER INFORMATION: Designed oligonucleotide based on mutant FRT
      sequence.

<400> SEQUENCE: 32
gaagttccta tactttctac agaataggaa cttc                               34

<210> SEQ ID NO 33
<211> LENGTH: 54
<212> TYPE: DNA
<213> ORGANISM: Artificial Sequence
<220> FEATURE:
<223> OTHER INFORMATION: Designed oligonucleotide based on FLP
      recognition sequence.

<400> SEQUENCE: 33
aaattccgga gaagttccta ttctctagaa agtataggaa cttcgacgtc attt         54

<210> SEQ ID NO 34
<211> LENGTH: 27
<212> TYPE: DNA
<213> ORGANISM: Artificial Sequence
<220> FEATURE:
<223> OTHER INFORMATION: Designed oligonucleotide as polylinker based on
      recognition sequences of SwaI, EcoRI, ScaI, KpnI and SmaI, in this
      order.

<400> SEQUENCE: 34
aaattgaatt cgagctcggt acccggg                                       27

<210> SEQ ID NO 35
<211> LENGTH: 18
<212> TYPE: DNA
<213> ORGANISM: Artificial Sequence
<220> FEATURE:
<223> OTHER INFORMATION: Designed oligonucleotide as linker based on
      sequence encoding BglII recognition sequence, two stop codons, and
      XhoI recoginition sequence.

<400> SEQUENCE: 35
gatcttacta gtaggatc                                                 18

<210> SEQ ID NO 36
<211> LENGTH: 18
<212> TYPE: DNA
<213> ORGANISM: Artificial Sequence
<220> FEATURE:
<223> OTHER INFORMATION: Designed oligonucleotide as linker based on
      sequence encoding BglII recognition sequence, two stop codons, and
      XhoI recoginition sequence.

<400> SEQUENCE: 36
tcgagatcct actagtaa                                                 18
```